(12) United States Patent
Chang et al.

(10) Patent No.: US 7,919,580 B2
(45) Date of Patent: Apr. 5, 2011

(54) POLYSACCHARIDE-PROTEIN BINDING MODEL AND NANO-FIBRIL FORMATION OF A STARCH BINDING DOMAIN

(75) Inventors: Margaret Dah-Tsyr Chang, Hsinchu (TW); Yuh-Ju Sun, Hsinchu (TW); Ping-Chiang Lyu, Hsinchu (TW); Shu-Chuan Lin, Hsinchu (TW); Wei-I Chou, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 58 days.

(21) Appl. No.: 12/359,035

(22) Filed: Jan. 23, 2009

(65) Prior Publication Data

US 2009/0186369 A1 Jul. 23, 2009

Related U.S. Application Data

(60) Provisional application No. 61/022,960, filed on Jan. 23, 2008.

(51) Int. Cl.
C07K 1/00 (2006.01)
C07K 14/00 (2006.01)
C12Q 1/40 (2006.01)
C12N 9/34 (2006.01)

(52) U.S. Cl. .................. 530/327; 530/300; 530/338
(58) Field of Classification Search .................. None
See application file for complete search history.

(56) References Cited

OTHER PUBLICATIONS

Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Liu W-T, Lin S-C, Chou W-I, Liu T-H, Pan R-L, Tzou D-L, Hua T-E, Chang M D-T, "Identification and characterization of a novel fibril forming peptide in fungal starch binding," Biochemical and Biophysical Research Communications, Dec. 2008, 377: 966-970. Available online Oct. 24, 2008.*
Ren Mikkelsen et al., A Novel Type Caroyhydrate-Binding Module Identified in Alpha-Glucan, Water Dikinases Is Specific for Regulated Plastidial Starch Metabolism, Biochemistry, 2006, pp. 4674-4682, 45.
O. Sumner Makin et al., Molecular basis for amyloid fibril formation and stability, PNAS, Jan. 11, 2005, pp. 315-320, vol. 102 No. 2.

* cited by examiner

*Primary Examiner* — Julie Ha
(74) *Attorney, Agent, or Firm* — WPAT, P.C.; Anthony King

(57) ABSTRACT

A polysaccharide-protein binding model of SBD, and a fibril-forming 14-residue peptide consisting of X1NNNX2X3NYQX4X5X6X7X8, wherein the X1 and X8 mean a pair of opposite charged amino acid residues, and the X2, X3, X4, X5, X6, or X7 means an amino acid residue is described. A mixture for diminising a polysaccharide, comprising at least two starch binding domains (SBDs) and a polysaccharide in a helix form is also presented. A method of providing an oligosaccharide, and a method of producing an amyloid-like fibril and use thereof are further described.

5 Claims, 15 Drawing Sheets

(A)

(B)

(C)

(A)

(B) (C)

(A)

(B)

(A)

(B)

(C)

(A)

(B)

(A)

(B)

(A)

(B)

SEQUENCE LISTING

<160> NUMBER OF SEQ ID NOS: 27

<210> SEQ ID NO 1
<211> LENGTH: 108
<212> TYPE: PRT
<213> ORGANISM: Rhizopus oryzae
<220> FEATURE:
<221> NAME/KEY: DOMAIN
<222> LOCATION: (1)..(108)

<400> SEQUENCE: 1

Ala Ser Ile Pro Ser Ser Ala Ser Val Gln Leu Asp Ser Tyr Asn Tyr
1               5                   10                  15

```
Asp Gly Ser Thr Phe Ser Gly Lys Ile Tyr Val Lys Asn Ile Ala Tyr
            20                  25                  30

Ser Lys Lys Val Thr Val Val Tyr Ala Asp Gly Ser Asp Asn Trp Asn
        35                  40                  45

Asn Asn Gly Asn Ile Ile Ala Ala Ser Phe Ser Gly Pro Ile Ser Gly
    50                  55                  60

Ser Asn Tyr Glu Tyr Trp Thr Phe Ser Ala Ser Val Lys Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: Modified SBD.
<220> FEATURE:
<221> NAME/KEY: MISC_FEATURE
<222> LOCATION: (1)..(107)

<400> SEQUENCE: 2

Ala Ser Ile Pro Ser Ser Ala Ser Val Gln Leu Asp Ser Tyr Asn Tyr
1               5                   10                  15

Asp Gly Ser Thr Phe Ser Gly Lys Ile Tyr Val Lys Asn Ile Ala Tyr
            20                  25                  30

Ser Lys Lys Val Thr Val Val Tyr Ala Asp Gly Ser Asp Asn Trp Asn
        35                  40                  45

Asn Asn Gly Asn Ile Ile Ala Ala Ser Phe Ser Gly Pro Ile Ser Gly
    50                  55                  60

Ser Asn Tyr Glu Tyr Trp Thr Phe Ser Ala Ser Val Lys Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser
            100                 105

<210> SEQ ID NO 3
<211> LENGTH: 108
<212> TYPE: PRT
<213> ORGANISM: Artificial Sequence
<220> FEATURE:
<223> OTHER INFORMATION: Modified SBD.
<220> FEATURE:
<221> NAME/KEY: MISC_FEATURE
<222> LOCATION: (1)..(108)

<400> SEQUENCE: 3

Ala Ser Ile Pro Ser Ser Ala Ser Val Gln Leu Asp Ser Tyr Asn Tyr
1               5                   10                  15

Asp Gly Ser Thr Phe Ser Gly Lys Ile Tyr Val Lys Asn Ile Ala Tyr
            20                  25                  30

Ser Lys Lys Val Thr Val Val Tyr Ala Asp Gly Ser Asp Asn Trp Asn
        35                  40                  45

Asn Asn Gly Asn Ile Ile Ala Ala Ser Phe Ser Gly Pro Ile Ser Gly
    50                  55                  60

Ser Asn Tyr Glu Tyr Trp Thr Phe Ser Ala Ser Val Lys Gly Ile Lys
65                  70                  75                  80
```

```
Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser Ala
                100                 105

<210> SEQ ID NO 4
<211> LENGTH: 108
<212> TYPE: PRT
<213> ORGANISM: Artificial Sequence
<220> FEATURE:
<223> OTHER INFORMATION: Modified SBD.
<220> FEATURE:
<221> NAME/KEY: MISC_FEATURE
<222> LOCATION: (1)..(108)

<400> SEQUENCE: 4

Ala Ser Ile Pro Ser Ser Ala Ser Val Gln Leu Asp Ser Tyr Asn Tyr
1               5                   10                  15

Asp Gly Ser Thr Phe Ser Gly Lys Ile Tyr Val Lys Asn Ile Ala Tyr
                20                  25                  30

Ser Lys Lys Val Thr Val Val Tyr Ala Asp Gly Ser Asp Asn Trp Asn
                35                  40                  45

Asn Asn Gly Asn Ile Ile Ala Ala Ser Phe Ser Gly Pro Ile Ser Gly
            50                  55                  60

Ser Asn Tyr Glu Tyr Trp Thr Phe Ser Ala Ser Val Lys Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser Arg
                100                 105

<210> SEQ ID NO 5
<211> LENGTH: 108
<212> TYPE: PRT
<213> ORGANISM: Artificial Sequence
<220> FEATURE:
<223> OTHER INFORMATION: Modified SBD.
<220> FEATURE:
<221> NAME/KEY: MISC_FEATURE
<222> LOCATION: (1)..(108)

<400> SEQUENCE: 5

Ala Ser Ile Pro Ser Ser Ala Ser Val Gln Leu Asp Ser Tyr Asn Tyr
1               5                   10                  15

Asp Gly Ser Thr Phe Ser Gly Lys Ile Tyr Val Lys Asn Ile Ala Tyr
                20                  25                  30

Ser Lys Lys Val Thr Val Val Tyr Ala Asp Gly Ser Asp Asn Trp Asn
                35                  40                  45

Asn Asn Gly Asn Ile Ile Ala Ala Ser Phe Ser Gly Pro Ile Ser Gly
            50                  55                  60

Ser Asn Tyr Glu Tyr Trp Thr Phe Ser Ala Ser Val Lys Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser His
                100                 105

<210> SEQ ID NO 6
<211> LENGTH: 108
<212> TYPE: PRT
<213> ORGANISM: Artificial Sequence
```

```
<220> FEATURE:
<223> OTHER INFORMATION: Modified SBD.
<220> FEATURE:
<221> NAME/KEY: MISC_FEATURE
<222> LOCATION: (1)..(108)

<400> SEQUENCE: 6

Ala Ser Ile Pro Ser Ser Ala Ser Val Gln Leu Asp Ser Tyr Asn Tyr
 1               5                   10                  15

Asp Gly Ser Thr Phe Ser Gly Lys Ile Tyr Val Lys Asn Ile Ala Tyr
            20                  25                  30

Ser Lys Lys Val Thr Val Val Tyr Ala Asp Gly Ser Asp Asn Trp Asn
        35                  40                  45

Asn Asn Gly Asn Ile Ile Ala Ala Ser Phe Ser Gly Pro Ile Ser Gly
    50                  55                  60

Ser Asn Tyr Glu Tyr Trp Thr Phe Ser Ala Ser Val Lys Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser Asp
            100                 105

<210> SEQ ID NO 7
<211> LENGTH: 14
<212> TYPE: PRT
<213> ORGANISM: Rhizopus oryzae
<220> FEATURE:
<221> NAME/KEY: SITE
<222> LOCATION: (1)..(14)

<400> SEQUENCE: 7

Asp Asn Asn Asn Ser Ala Asn Tyr Gln Val Ser Thr Ser Lys
 1               5                   10

<210> SEQ ID NO 8
<211> LENGTH: 13
<212> TYPE: PRT
<213> ORGANISM: Rhizopus oryzae
<220> FEATURE:
<221> NAME/KEY: SITE
<222> LOCATION: (1)..(13)

<400> SEQUENCE: 8

Asp Asn Asn Asn Ser Ala Asn Tyr Gln Val Ser Thr Ser
 1               5                   10

<210> SEQ ID NO 9
<211> LENGTH: 13
<212> TYPE: PRT
<213> ORGANISM: Rhizopus oryzae
<220> FEATURE:
<221> NAME/KEY: SITE
<222> LOCATION: (1)..(13)

<400> SEQUENCE: 9

Asn Asn Asn Ser Ala Asn Tyr Gln Val Ser Thr Ser Lys
 1               5                   10

<210> SEQ ID NO 10
<211> LENGTH: 12
<212> TYPE: PRT
<213> ORGANISM: Rhizopus oryzae
<220> FEATURE:
<221> NAME/KEY: SITE
<222> LOCATION: (1)..(12)
```

-continued

```
<400> SEQUENCE: 10

Asn Asn Asn Ser Ala Asn Tyr Gln Val Ser Thr Ser
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 11

Lys Asn Asn Asn Ser Ala Asn Tyr Gln Val Ser Thr Ser Lys
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 12

Ala Asn Asn Asn Ser Ala Asn Tyr Gln Val Ser Thr Ser Lys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 13

Asp Ala Asn Asn Ser Ala Asn Tyr Gln Val Ser Thr Ser Lys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 14

Asp Asn Ala Asn Ser Ala Asn Tyr Gln Val Ser Thr Ser Lys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)
```

-continued

```
<400> SEQUENCE: 15

Asp Asn Asn Ala Ser Ala Asn Tyr Gln Val Ser Thr Ser Lys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 16

Asp Asn Asn Asn Ala Ala Asn Tyr Gln Val Ser Thr Ser Lys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 17

Asp Asn Asn Asn Ser Ala Ala Tyr Gln Val Ser Thr Ser Lys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 18

Asp Asn Asn Asn Ser Ala Asn Ala Gln Val Ser Thr Ser Lys
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 19

Asp Asn Asn Asn Ser Ala Asn Tyr Ala Val Ser Thr Ser Lys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)
```

```
<400> SEQUENCE: 20

Asp Asn Asn Asn Ser Ala Asn Tyr Gln Ala Ser Thr Ser Lys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 21

Asp Asn Asn Asn Ser Ala Asn Tyr Gln Val Ala Thr Ser Lys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 22

Asp Asn Asn Asn Ser Ala Asn Tyr Gln Val Ser Ala Ser Lys
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 23

Asp Asn Asn Asn Ser Ala Asn Tyr Gln Val Ser Thr Ala Lys
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 24

Asp Asn Asn Asn Ser Ala Asn Tyr Gln Val Ser Thr Ser Ala
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)
```

```
<400> SEQUENCE: 25

Asp Asn Asn Asn Ser Ala Asn Tyr Gln Val Ser Thr Ser Asp
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 26

Ala Asn Asn Asn Ser Ala Asn Tyr Gln Val Ser Thr Ser Ala
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Mutant CT-14 peptides.
<220> FEATURE:
<221> NAME/KEY: MISC_FEATURE
<222> LOCATION: (1)..(14)

<400> SEQUENCE: 27

Lys Asn Asn Asn Ser Ala Asn Tyr Gln Val Ser Thr Ser Asp
1               5                   10
```

POLYSACCHARIDE-PROTEIN BINDING MODEL AND NANO-FIBRIL FORMATION OF A STARCH BINDING DOMAIN

CROSS-REFERENCE TO RELATED APPLICATIONS

This application claims priority to a Provisional Application (Application No. 61/022,960) filed on Jan. 23, 2008, which is hereby incorporated by reference in its entirety.

Although incorporated by reference in its entirety, no arguments or disclaimers made in the parent application apply to this Non-provisional application. Any disclaimer that may have occurred during the prosecution of the above-referenced application(s) is hereby expressly rescinded. Consequently, the Patent Office is asked to review the new set of claims in view of all the prior art of record and any search that the Office deems appropriate.

FIELD OF THE INVENTION

The present invention relates to a starch binding domain, a polysaccharide-protein binding model, and a fibril forming peptide for amyloid-like fibril formation. This invention further relates to a nanotube comprising the fibril forming peptide.

BACKGROUND OF THE INVENTION

Starch, the primary source of stored energy in plants, is composed of amylose and amylopectin. The former consists almost entirely of α-(1,4)-D-glucopyranose units; however, a few α-1,6 branches and linked phosphate groups may be found. The latter is composed of α-(1,4)-D-glucose segments connected by about 5% α-1,6 branching sites. Both amylose and amylopectin fold into helical structures and are further organized into the semicrystalline granular form.

Glucoamylase (GA), also known as amyloglucosidase or γ-amylase (EC 3.2.1.3), is a biocatalyst capable of hydrolyzing a-1,4 and a-1,6 glycosidic linkages in raw starches and related oligosaccharides to produce β-D-glucose (Sauer J, Sigurskjold B W, Christensen U, Frandsen T P, Mirgorodskaya E, Harrison M, Roepstorff P, Svensson B: Glucoamylase: structure/function relationships, and protein engineering. Biochim. Biophys. Acta., 1543 (2000)275-293; Norouzian D, Akbarzadeh A, Scharer J M, Moo Young M: Fungal glucoamylases. Biotechnol Adv, 24 (2006) 80-85). The GA (1,4-α-D-glucan glucohydrolase, EC 3.2.1.3, GA) of *R. oryzae* (RoGA) contains two functional domains, an N-terminal starch-binding domain (SBD) and a C-terminal catalytic domain connected by an O-glycosylated interdomain linker. The C-terminal catalytic domain is classified as a member of the glycoside hydrolase family 15 (GH15), and the SBD is a member of the family 21 carbohydrate binding modules (RoGACBM21) as defined by CAZY database.

SBDs can be functionally independent of the catalytic domains and have been proposed to increase the hydrolysis of granular starch by disrupting its structure and concentrating the catalytic domains on the surface of starch. Ligand binding of RoGACBM21 with starch and soluble oligosaccharides was determined by Chang (W. I. Chou, T. W. Pai, S. H. Liu, B. K. Hsiung, M. D. Chang, The family 21 carbohydrate-binding module of glucoamylase from *Rhizopus oryzae* consists of two sites playing distinct roles in ligand binding, Biochem. J. 396 (2006) 469-477). The $K_d$ values were of a similar order of magnitude to that of CBM20 from *Aspergillus niger* glucoamylase (AnGA), but the maximal amount of bound protein ($B_{max}$) of RoGACBM21 was 40-70-fold higher than that of AnGACBM20. The binding affinity between RoGACBM21 and soluble ligands, βCD (β-cyclodextrin) and G7 (maltoheptaose), was measured as approximately 5 μM.

Under normal condition, the SBD of RoGA consists of eight β-strands and two functional sites, which perform distinct roles in ligand binding (W. I. Chou, T. W. Pai, S. H. Liu, B. K. Hsiung, M. D. Chang, The family 21 carbohydrate-binding module of glucoamylase from *Rhizopus oryzae* consists of two sites playing distinct roles in ligand binding, Biochem. J. 396 (2006) 469-477; Y. N. Liu, Y. T. Lai, W. I. Chou, M. D. Chang, P. C. Lyu, Solution structure of family 21 carbohydrate-binding module from *Rhizopus oryzae* glucoamylase, Biochem. J. 403 (2007) 21-30; J. Y. Tung, M. D. Chang, W. I. Chou, Y. Y. Liu, Y. H. Yeh, F. Y. Chang, S. C. Lin, Z. L. Qiu, Y. J. Sun, Crystal structures of starch binding domain from *Rhizopus oryzae* glucoamylase reveal a polysaccharide binding path, Biochem J, 416 (2008) 27-36). Interestingly, the recombinant SBD of 108 amino acid residues adopts stronger β conformation upon heat denaturation, a phenomenon similar to the reported heat treatment, ordered β-amyloid-like fibril formation of hen egg white lysozyme and acidic fibroblast growth factor (Srisailam, S., Wang, H. M., Kumar, T. K., Rajalingam, D., Sivaraja, V, Sheu, H. S., Chang, Y. C. and Yu, C. (2002) Amyloid-like fibril formation in an all beta-barrel protein involves the formation of partially structured intermediate(s). J. Biol. Chem. 277, 19027-19036). Because native SBD and acidic fibroblast growth factor both contain all β-barrel structures, whether or not the chemical and biophysical mechanisms underlying the thermo-induced conformational changes of SBD was similar to those of acidic fibroblast growth factor were investigated.

To date, 53 CBM families have been classified, and eight of them (families 20, 21, 25, 26, 34, 41, 45, and 48) have starch binding activity. The dissociation constants $K_d$ for the binding of SBDs to starch are in the micromolar range. However, SBDs associated with GA only appear in two families (CBM20 and CBM21). Previous reports on structure-based molecular modeling and nuclear magnetic resonance (NMR) spectroscopy of RoGACBM21 (Y. N. Liu, Y. T. Lai, W. I. Chou, M. D. Chang, P. C. Lyu, Solution structure of family 21 carbohydrate-binding module from *Rhizopus oryzae* glucoamylase, Biochem. J. 403 (2007) 21-30) revealed that although these two families share a very low sequence identity, they indeed have similar biological function and structural folding. Therefore, the most recent evolutionary study on CBM20 and CBM21 proposes grouping these two SBD families into a new CBM clan (Machovic, M. & Janecek, S. The evolution of putative starch-binding domains. FEBS Lett 580, (2006) 6349-56; Machovic, M. & Janecek, S. Starch-binding domains in the post-genome era. Cell Mol Life Sci 63, (2006) 2710-24). However, the detailed binding mechanisms between CBM21 and starch/glycogen remain unclear.

CBM45

The CBM45 family has originated from eukaryotic proteins from the plant kingdom as the N-terminal modules of plastidial α-amylases and α-glucan water dikinases. The N-terminally positioned motif of potato α-glucan water dikinase (GWD, EC 2.7.9.4) has been demonstrated to be specific for plastidial α-glucan degradation and plays a pivotal role in starch metabolism (Mikkelsen, R., Suszkiewicz, K. & Blennow, A. A novel type carbohydrate-binding module identified in alpha-glucan, water dikinases is specific for regulated plastidial starch metabolism. Biochemistry 45, (2006) 4674-82). This type of SBD usually occurs as tandem repeats containing conserved tryptophans, which are responsible for carbohydrate binding. The three-dimensional structure of a CBM45 motif has not yet been determined.

CBM48

The CBM48 family is the most recently established starch-binding CBM. It contains approximately 100 amino acid residues associated with GH13 modules. This family covers a number of archaeal amylase and glycogen debranching enzymes, bacterial amylases and pullulanases branching-enzymes, and even eukaryotic AMP-activated protein kinases (AMPK) (Parker, G. J., Koay, A., Gilbert-Wilson, R., Waddington, L. J. & Stapleton, D. AMP-activated protein kinase does not associate with glycogen alpha-particles from rat liver. Biochem Biophys Res Commun 362, (2007) 811-5). Interestingly, the glycogen-binding function has been demonstrated.

Three-dimensional structures of several CBM superfamilies have been reported: CBM20 from AnGA, CBM21 from RoGA, CBM25 and CBM26 from *Bacillus halodurans* maltohexaose-forming amylase, CBM34 from *Thermoactinomyces vulgaris* α-amylase (TvAI), CBM41 from *Klebsiella aerogenes* pullulanase, and CBM48 from *Rattus norvegicus* AMP-activated protein kinase.

In general, at temperatures above thermal stability, denatured proteins may exist in a partially structured nucleated state(s), permitting them to cooperatively interact with one another to form the ordered amyloid-like fibrils and to establish a nucleated polymerization mechanism (S. Srisailam, H. M. Wang, T. K. Kumar, D. Rajalingam, V. Sivaraja, H. S. Sheu, Y. C. Chang, C. Yu, Amyloid-like fibril formation in an all beta-barrel protein involves the formation of partially structured intermediate(s), J. Biol. Chem. 277 (2002) 19027-19036) Numerous soluble proteins being able to convert to insoluble amyloid-like fibrils have common properties. For initiation and stabilization of amyloid-like fibrils derived from particular proteins or polypeptides, π-bonding between adjacent aromatic rings and salt bridges between charge pairs have been suggested to play crucial roles (A. T. Petkova, Y. Ishii, J. J. Balbach, O. N. Antzutkin, R. D. Leapman, F. Delaglio, R. Tycko, A structural model for Alzheimer's beta-amyloid fibrils based on experimental constraints from solid state NMR, Proc. Natl. Acad. Sci. U.S.A. 99 (2002) 16742-16747; L. Tjernberg, W. Hosia, N. Bark, J. Thyberg, J. Johansson, Charge attraction and beta propensity are necessary for amyloid fibril formation from tetrapeptides, J. Biol. Chem. 277 (2002) 43243-43246; O. S. Makin, E. Atkins, P. Sikorski, J. Johansson, L. C. Serpell, Molecular basis for amyloid fibril formation and stability, Proc. Natl. Acad. Sci. U.S.A. 102 (2005) 315-320). In addition, high protein concentrations, incompatible ionic strength, extreme pH and temperature can also influence fibril formation.

Nanotechnology has recently become of great interest for a variety of reasons. For example, nanostructures may be used to generate devices at a molecular level, thereby permitting molecular-level probing. Specifically, it has been suggested that fibrils can be used for connectors, wires, and actuators. Additionally, it has been suggested that nanotubes may be used as miniature pipettes for introducing small proteins into biological or other systems. It is worthwhile to note, however, that peptide-based nanotube structure is more robust and stable than lipid-based nanotubes.

SUMMARY OF THE INVENTION

Figure 1:
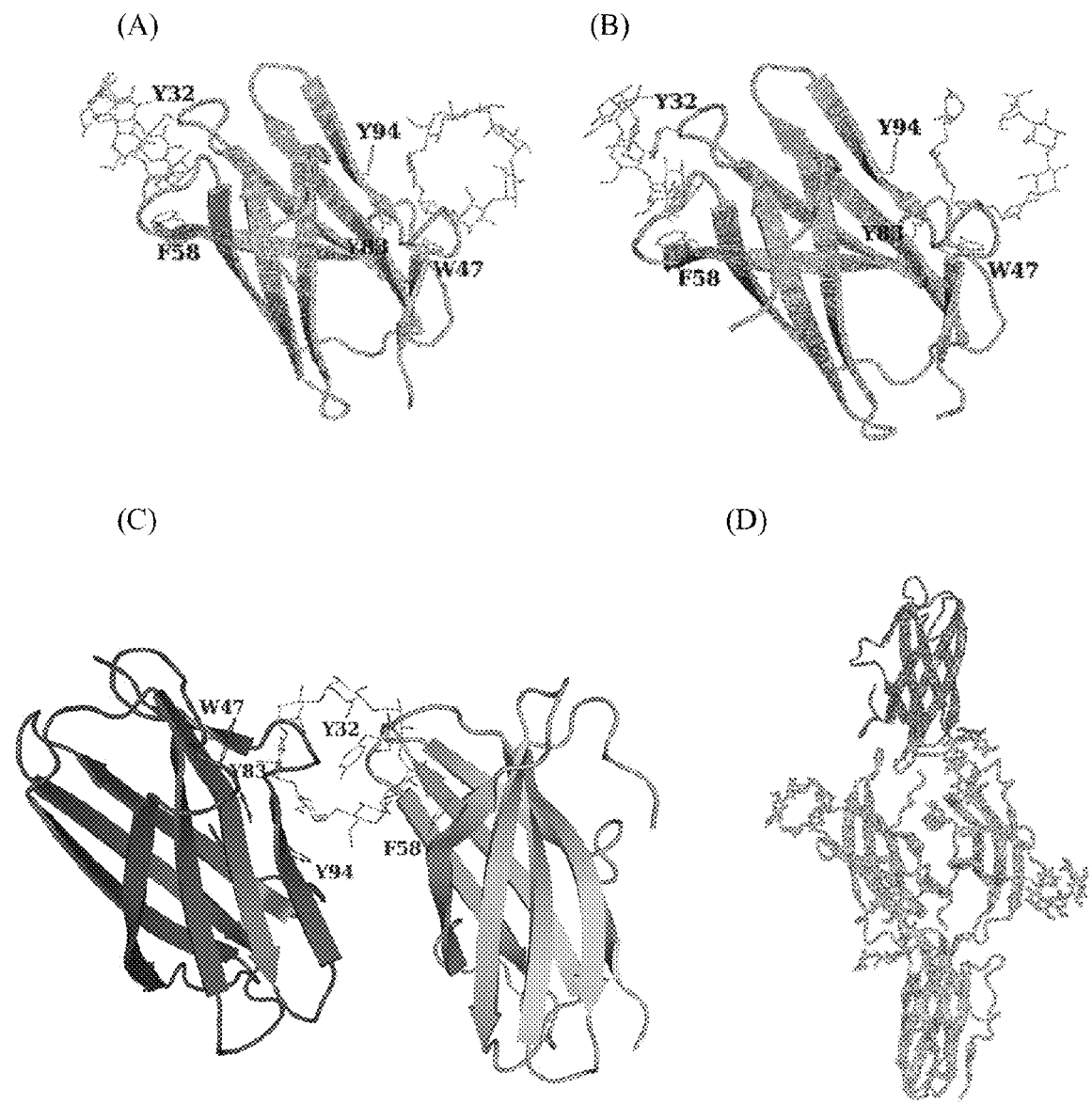
FIG. 1(A) shows a ribbon diagram of the RoGACBM21-βCD complex. Eight strands are labeled as 1-8 and βCD are shown in sticks. (B) shows a ribbon diagram of the RoGACBM21-G7 complex. Maltoheptaoses are shown in sticks. (C) shows the RoGACBM21-βCD complex with one βCD and two RoGACBM21 molecules. The key aromatic residues, Trp47, Tyr83, and Tyr94 (site I) as well as Tyr32 and Phe58 (site II) are shown in sticks. (D) shows the RoGACBM21-G7 complex. The maltoheptaoses are shown in sticks.

The present invention relates to a mixture for diminising a polysaccharide, comprising at least two starch binding domains (SBDs) and a polysaccharide in a helix form. The present invention also relates to a method of providing an oligosaccharide comprising (a) providing a composition comprising a SBD linked to a catalytic domain by a linker, wherein the linker consists of at least 2 amino acid residues; and (b) mixing the composition with a polysaccharide in a buffer in which the catalytic domain is activated. The present invention further relates to a fibril-forming 14-residue peptide consisting of $X_1NNNX_2X_3NYQX_4X_5X_6X_7X_8$, wherein the $X_1$ and $X_8$ mean a pair of opposite charged amino acid residues, and the $X_2$, $X_3$, $X_4$, $X_5$, $X_6$, or $X_7$ means an amino acid residue. The present invention further relates to a method of producing an amyloid-like fibril, comprising dissolving the peptide of claim 12 in a solution with pH value ranges from 4.0 to 7.0 upon heat treatment for mature fibril formation.

DETAILED DESCRIPTION OF THE INVENTION

The present invention provides a mixture for diminising a polysaccharide, comprising at least two starch binding domains (SBDs) and a polysaccharide in a helix form. In a preferred embodiment, the polysaccharide is an amylose or amylopectin aggregate; and the number of SBDs is three to four wherein the SBD is derived from carbohydrate binding module (CBM) family 20, 21, 25, 26, 34, 41, 45, or 48;

In a more preferred embodiment, the SBD is derived from glucoamylase (GA) of *Rhizopus oryzae*, and further linked to a catalytic domain by a linker. In another embodiment, the SBD is linked to a fluorescent material, and is applied to quantitative detection of polysaccharides.

The present invention also provides a method of providing an oligosaccharide comprising (a) providing a composition comprising a SBD linked to a catalytic domain by a linker, wherein the linker consists of at least 2 amino acid residues; and (b) mixing the composition with a polysaccharide in a buffer in which the catalytic domain is activated.

The term "oligosaccharide" used herein means an oligosaccharide having 3 to 15 unit length of glucose; preferably, the oligosaccharide has 5 to 12 unit length; and most preferably, the oligosaccharide has 7 to 10 unit length.

The term "linker" used herein means at least 2 amino acid residues which are between a SBD and a catalytic domain and linking them together; preferably, the linker consists of 2 to 60 amino acid residues.

In a preferred embodiment, the catalytic domain comprises α-amylase, β-amylase, cyclodextrin glycosyltransferase, cyclodextrin glucanotransferase, cyclomaltodextrinase, acarviosyl transferase, 6-α-glucosyltransferase, 4-α-glucanotransferase, α-1,6-cyclomaltopentaose-forming glucanotransferase, pullulanase, maltohexaose-forming α-amylase, maltopentaose-forming amylase, maltotriose-forming α-amylase, maltotetraose-forming amylase, glucoamylase, maltogenic α-amylase, neopullulanase, α-glucosidase, maltooligosyltrehalose trehalohydrolase, isoamylase, 1,4-α-glucan branching enzyme, glycogen-debranching enzyme, or starch branching enzyme.

In another embodiment, the SBD is further linked to a fluorescent material and is applied to quantitate polysaccharides by detecting fluorescent brightness.

The present invention further provides a fibril-forming 14-residue peptide consisting of $X_1NNNX_2X_3NYQX_4X_5X_6X_7X_8$, wherein the $X_1$ and $X_8$ mean a pair of opposite charged amino acid residues, and the $X_2$, $X_3$, $X_4$, $X_5$, $X_6$, or $X_7$ means an amino acid residue. In a preferred embodiment, the pair of opposite charged amino acid residues consists of positively charged residue K, R, or H; and negatively charged residue D or E. In a preferred embodiment, the $X_1$ is D when $X_8$ is K; the $X_1$ is K when $X_8$ is D; the $X_2$ is S or A; the $X_3$ is A; the $X_4$ is V or A; the $X_5$ is S or A; the $X_6$ is T or A; and the $X_7$ is S or A. In the most preferred embodiment, the fibril-forming 14-residue peptide is SEQ ID NO: 7.

The present invention further provides a method of producing an amyloid-like fibril, comprising dissolving the fibril-forming 14-residue peptide in a solution with pH value ranges from 4.0 to 7.0 upon heat treatment for mature fibril formation. In a preferred embodiment, the solution is 10 mM sodium-citrate or phosphate-citrate buffer; and the heat temperature is at least at 37° C.

The fibril can be applied to carbohydrate separation, drug delivery, biodegradable three-dimensional scaffold construction, nanowire production, or nanotube formation.

The fibril further forms a nanotube which has the formula: $X_n-[(P_{14})_m-L_q]_r-Y_s$ wherein $P_{14}$ means the 14-residue peptide of SEQ ID NO:7; L, X and Y represent peptides or metal; $m$, $n$, $q$, $r$ and $s$ are constants. In a preferred embodiment, X and Y of formula can be further linked with peptides or metal.

The nanotube can be applied to filtration systems or used as miniature pipettes for introducing small proteins into biological or other systems.

EXAMPLES

The examples below are non-limiting and are merely representative of various aspects and features of the present invention.

Example 1

Protein Expression and Purification

Recombinant enzyme expression, purification, and functional assay for RoGACBM21 had been reported (W. I. Chou, T. W. Pai, S. H. Liu, B. K. Hsiung, M. D. Chang, The family 21 carbohydrate-binding module of glucoamylase from *Rhizopus oyrzae* consists of two sites playing distinct roles in ligand binding, Biochem. J. 396 (2006) 469-477). Briefly, the DNA fragment encoding RoGACBM21 was cloned into the pET23a(+) expression vector and overexpressed in *E. coli* BL21-Gold (DE3) cells (Novagen). Recombinant SBD sample was purified by His-Bind® affinity column chromatography (Novagen) using the standard protocol. The purified SBD sample was dialyzed against sodium acetate buffer (50 mM, pH 5.5). The resulting C-terminally 6× His-tagged SBD (11.65 kDa) was purified by Ni-NTA affinity chromatography with a final yield of 5 mg of purified protein per liter of cells.

Site-directed Mutagenesis

All RoGACBM21 mutants were generated using PCR-based QuikChange site-directed mutagenesis method (Stratagene) as previously described with pET-RoGACBM21 as the template, two complementary primers containing the desired mutation, and Pfu Turbo DNA polymerase (Stratagene) were added. All constructs were transformed into competent *E. coli* BL21-Gold (DE3) for protein expression.

Quantitative Measurement of Binding to Starch

The starch binding isotherm was analyzed as a saturation binding assay as reported. Wild-type and mutant RoGACBM21 derivatives (100 μL, in 50 mM sodium acetate, pH 5.5) were mixed with 0.1 mg of prewashed insoluble starch and incubated at 25° C. with gentle stirring for 16 h. After centrifugation at 16,000×g for 10 min at 4° C., the protein concentration of the supernatant (unbound protein) was determined by BCA assay, and the amount of bound protein was calculated from the difference between the initial and unbound protein concentrations. The $K_d$ and $B_{max}$ values were determined by fitting to the non-linear regression of the binding isotherms using a standard single-site binding model.

Quantitative Measurement of Binding to Soluble Carbohydrate

Fluorescence spectrophotometry of the binding of wild-type or mutant RoGACBM21 to βCD was recorded by measuring changes in the intrinsic protein fluorescence intensity. Experiments were performed in 50 mM sodium acetate, pH 5.5, at 25° C. using a PerkinElmer LS-55 spectrophotometer. Circular and linear carbohydrates (2 to 20 mM) were titrated into RoGACBM21 (1 μM, 2 mL), and the fluorescence-emission spectrum was monitored at 350 nm with a fixed excitation at 280 nm. The relative changes in fluorescence intensity were plotted against ligand concentration, and the data were fitted to a simulated curve using the appropriate equation for a single binding site.

Crystallization

Crystallization trials were carried out by the hanging-drop vapor-diffusion method. Both protein (1 μL) and reservoir (1 μL) solution were mixed and equilibrated against a reservoir solution (500 μL) in Linbro plates. Initial crystallization conditions were obtained using Hampton Research Crystal Screen kits and then further optimized to obtain diffraction-quality crystals. The concentration of the RoGACBM21 used in crystallization was about 10 mg/mL. The cyclic carbohydrate, βCD, and linear carbohydrate, maltoheptaose, were respectively used with a molar ratio of 1:2 (protein:carbohydrates) to form SBD-βCD and SBD-G7 complexes. The SBD-βCD complex crystals grew to maximum dimensions of 0.1×0.1×0.3 mm within 3 days at 293 K using 18% PEG 8000 and 0.2 M zinc acetate in 0.1 M sodium cacodylate buffer (pH 6.5). The SBD-G7 complex crystals were grown from 30% PEG 8000 and 0.6 M ammonia sulfate at 293 K within 4 days to maximum dimensions of 0.1×0.1×0.2 mm.

X-ray Data Collection

The X-ray diffraction data of SBD-βCD and SBD-G7 complex crystals were collected at beamline BL13C1 in NSRRC (Taiwan, ROC). The data were processed and scaled using the program HKL2000. The SBD-βCD complex crystal diffracted to 1.8 Å and belongs to the rthorhombic $P2_12_12_1$ space group (Table 1).

TABLE 1

X-ray diffraction data and refinement statistics of SBD-βCD and SBD-G7 complexes

| | Crystal | |
|---|---|---|
| | SBD-βCD complex | SBD-G7 complex |
| Resolution (Å) | 1.8 | 2.3 |
| Space group | $P2_12_12_1$ | $P2_1$ |
| Unit cell (a/b/c) (Å) | 42.6/42.7/70.1 | 37.7/110.9/61.2 $\beta = 90.7°$ |
| Number of reflections collected | 54,409 | 76,379 |
| Number of unique reflections | 12,310 | 22,511 |
| Completeness (%) | 99.1 | 99. |
| I/σ (I) | 41.3 | 14.3 |
| $R_{merge}$ (%) | 3.3 | 7.8 |

The $V_M$ was calculated as 2.44 Å³Da⁻¹, with one molecule per asymmetric unit. The SBD-G7 complex crystal diffracted to 2.3 Å and belongs to the monoclinic $P2_1$ space group (Table 1). The $V_M$ was calculated as 2.46 Å³ Da⁻¹, with four molecules per asymmetric unit.

Structural Determination and Refinement

The structures of the SBD-βCD complex were determined using the unliganded solution structure of RoGACBM21 (PDB:2djm) as a search model by molecular replacement. The molecular replacement program MOLREP was used for the phase determination. Data between 8.0 to 4.0 Å and a Patterson radius of 20 Å were used to calculate the rotation and translation functions. Significant rotation and translation solutions were obtained for the SBD-βCD complex. After rigid body refinement, the correlation coefficient and R-factor were 31.7% and 54.7%, respectively. A similar procedure was applied for the structure determination of the SBD-G7 complex using the structure of SBD-βCD as a search model. Structural model building was carried out using XTALVIEW, and the structural refinement was performed by CNS. The final statistics of structural refinement for SBD-βCD and SBD-G7 complexes were summarized in Table 1. FIGS. 1-5 were produced with PYMOL.

PDB Accession Numbers

The coordinates of the RoGACBM21 complexes had been deposited in the PDB accession numbers 2v81 and 2v8m for SBD-βCD and SBD-G7 complexes, respectively.

Carbohydrate Binding Module Folding Topology

Several CBM superfamilies, including CBM20, CBM21, CBM25, CBM26, CBM34, CBM41, and CBM48, contained SBD in either the N- or C-terminal domain. These SBDs revealed low sequence identity but a similar immunoglobulin-like folding topology. RoGACBM21 had an extremely low identity (<15%) to AnGACBM20 as well as that of other SBD-containing CBM families. A structure-based multiple sequence alignment of SBDs from seven CBM superfamilies except CBM45, including RoGACBM21 from RoGA, AnGACBM20 from AnGA, BhCBM25 and BhCBM26 from *B. halodurans*, TvAICBM34 from *T. vulgaris*, KaCBM41 from *K. aerogenes*, and RnCBM48 from *R. norvegicus* based on the overall structural folding of eight strands of SBDs and the corresponding binding sites has been constructed (J. Y. Tung, M. D. Chang, W. I. Chou, Y. Y. Liu, Y. H. Yeh, E. Y. Chang, S. C. Lin, Z. L. Qiu, Y. J. Sun, Crystal structures of starch binding domain from *Rhizopus oryzae* glucoamylase reveal a polysaccharide binding path, Biochem J, 416 (2008) 27-36). It has been found that two types of topologies, type I and type II of SBDs, shared a similar overall structure by switching between the first and last β strands. Superfamilies CBM20, CBM25, CBM26 and CBM41 belonged to the type I topology, whereas CBM21, CBM34, and CBM48 belonged to type II topology.

Overall Structures

The crystal structures of RoGACBM21 in complex with a βCD (SBD-βCD) and with a maltoheptaose (SBD-G7) were determined at 1.8 and 2.3 Å, respectively. Both complexes (FIGS. 1A and 1B) shared very similar overall structures and folded into a compact domain of approximate dimensions of 28 Å×30 Å×42 Å. The overall structure of RoGACBM21 belonged to a typical β-sandwich fold with an immunoglobulin-like architecture. The β-sandwich was symmetric and composed of eight β strands, which were antiparallel except the last two strands. These strands paired as four hairpin β strands, β12, β34, β45, and β67/8, and folded as a β barrel (FIG. 1A). The β barrel contained a substantial hydrophobic core that contributed the major stabilization force for RoGACBM21.

Two carbohydrate binding sites, designated as sites I and II, were observed in both SBD-βCD and SBD-G7 complexes, in which sugar ligands, βCD and G7, were located at the almost diagonal ends of the surface of RoGACBM21 (FIGS. 1A and 1B) with a perpendicular orientation. Binding site I was located at Trp47 around loop β34, and site II was located at Tyr32 around loop β23 (FIG. 1). The carbohydrate binding ratio for both SBD-βCD and SBD-G7 complexes was one sugar ligand per SBD molecule (FIG. 1). However, RoGACBM21 shared each binding site with the neighboring molecule, and two RoGACBM21 molecules held one sugar ligand together (FIG. 1C).

Binding Sites

Site I was mainly comprised by three conserved aromatic residues, Trp47, Tyr83, and Tyr94, to form a broad, flat, and stable hydrophobic environment. The aromatic rings of these residues made up the binding curvature of SBD and interacted with the sugar rings of the ligand by ideal hydrophobic stacking interactions (J. Y. Tung, M. D. Chang, W. I. Chou, Y. Y. Liu, Y. H. Yeh, F. Y. Chang, S. C. Lin, Z. L. Qiu, Y. J. Sun, Crystal structures of starch binding domain from *Rhizopus oryzae* glucoamylase reveal a polysaccharide binding path, Biochem J, 416 (2008) 27-36). Trp47 in loop β34 underwent a conformational change upon carbohydrate binding. Site I was rather fixed because Tyr83 and Tyr94 were located in β6 and β7, respectively. Besides the hydrophobic interaction, several asparagine residues provided the hydrophilic interactions. Two unique polyN loops made by consecutive asparagines, Asn48-Asn49-Asn50 (loop β34) and Asn96-Asn97-Asn98-Asn101 (loop β78), were involved in ligand binding as well. The polyN loops grabbed the βCD molecule on two sides and assisted βCD to turn into the correct orientation to make hydrophobic binding with Trp47, Tyr83, and Tyr94. In particular, residues Asn50, Asn96, and Asn101 formed direct hydrogen bonds with βCD. These extra interactions from the polyN loops produced a higher binding capacity for RoGACBM21 as compared with those of other CBM superfamilies. Meanwhile, these polyN loops were also observed in other CBM21 GA superfamilies such as McGACBM21 from *Mucor circinelloides*.

Site II was generally formed by loops β23 and β45, particularly dominated by two aromatic residues, Tyr32 and Phe58. Nevertheless, both Tyr32 and Phe58 were in proximity to the sugar ring where the van der Waals surface and the βCD were closely packed. The sugar ring of βCD was nearly parallel to the ring of Tyr32, which protruded into the nonpolar cavity of βCD and formed a hydrogen bond with βCD O27 (J. Y. Tung, M. D. Chang, W. I. Chou, Y. Y. Liu, Y. H. Yeh, F. Y. Chang, S. C. Lin, Z. L. Qiu, Y. J. Sun, Crystal structures of starch binding domain from *Rhizopus oryzae* glucoamylase reveal a polysaccharide binding path, Biochem J, 416 (2008) 27-36). This unique binding was only observed in the SBD-βCD complex, and the β-glucan chains of βCD wrapped around Tyr32 to stabilize the binding. Similar binding patterns were observed in cyclodextrin glycosyltransferase and the glycogen binding domain of AMP-activated protein kinase; in which the corresponding residues were Leu600 and Leu146, respectively. Another key residue in site II was Phe58 whose hydrophobic phenyl ring formed a flat stacking interaction onto the sugar ring of glucosyl unit of βCD. Two planar rings of Tyr32 and Phe58 packed closely against the van der Waals surface of the βCD molecule and acted like a clamp to pick up the βCD. In addition to the hydrophobic interactions, residues Asn29, Lys34, and Glu68 supplied several hydrogen bond interactions with βCD. These residues interacted with each other by hydrogen bonds to provide a firm binding environment for βCD binding and also contributed the forces to stabilize the loops β23 and β45 of RoGACBM21. The binding area of site II was small and narrow and it protruded out more than that of site I.

The SBD-G7 complex with four molecules per asymmetric unit was shown in FIG. 1D. The overall structures of four SBDs were very similar with RMSD values of 0.57-1.04 Å in Cα. Four maltoheptaose ligands of the SBD-G7 complex were superimposed (J. Y. Tung, M. D. Chang, W. I. Chou, Y. Y. Liu, Y. H. Yeh, F. Y. Chang, S. C. Lin, Z. L. Qiu, Y. J. Sun, Crystal structures of starch binding domain from *Rhizopus oryzae* glucoamylase reveal a polysaccharide binding path, Biochem J, 416 (2008) 27-36). The key aromatic residues, Trp47, Tyr83, Tyr94, and Phe58 were in the same orientations except for Tyr32, which was still located in the center of G7 of the SBD-G7 complex, but not in the same orientation. The conformations of these maltoheptaoses were varied; however, they tended to fold into a U shape and fit the binding curvature of RoGACBM21. The major conformational difference appeared to be located in the two ends of maltoheptaose molecules. Therefore, the SBD-βCD and SBD-G7 complexes showed that SBD had a stable binding environment to accommodate a variety of sugars with different conformations and lengths.

Liganded and Unliganded RoGACBM21

Figure 2:
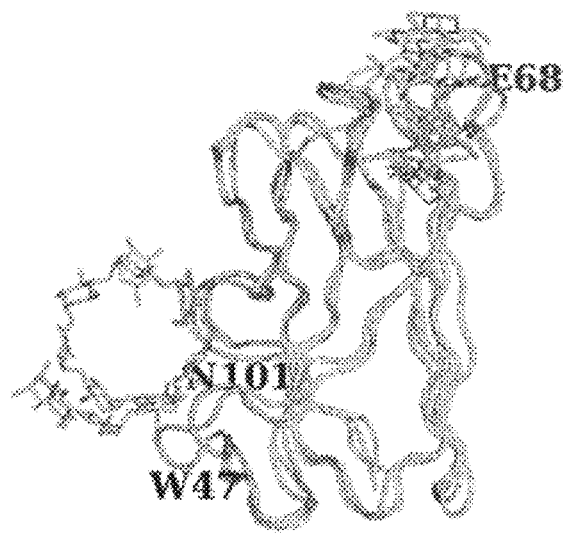
FIG. 2(A) shows three major structural differences among liganded and unliganded RoGACBM21 are labeled as Trp47, Glu68, and Asn101. (B) shows superimposition of the sugar binding sites of the SBD-βCD complex, the SBD-G7 complex, and the unliganded SBD. The key hydrophobic residues, Tyr32, Trp47, Phe58, Tyr83, and Tyr94, involved in binding are drawn in sticks. (C) shows superimposition of the sugar binding sites of the SBD-βCD complex, the SBD-G7 complex, and the unliganded SBD. The key hydrophilic residues, N29, K34, N50, E68, N96, and N101, involved in binding are drawn in sticks.
Figure 2:
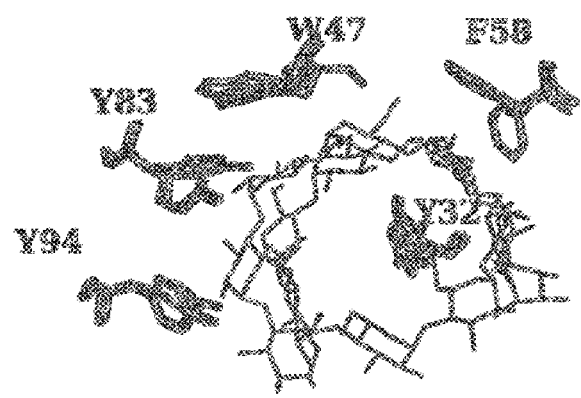
Figure 2:
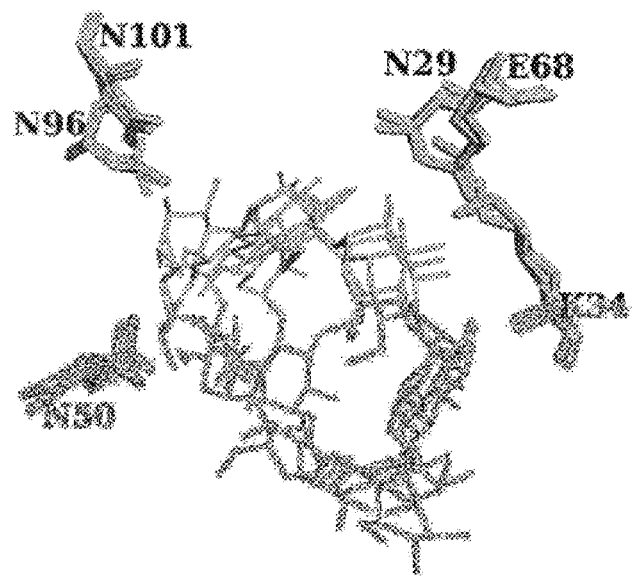
Figure 3:
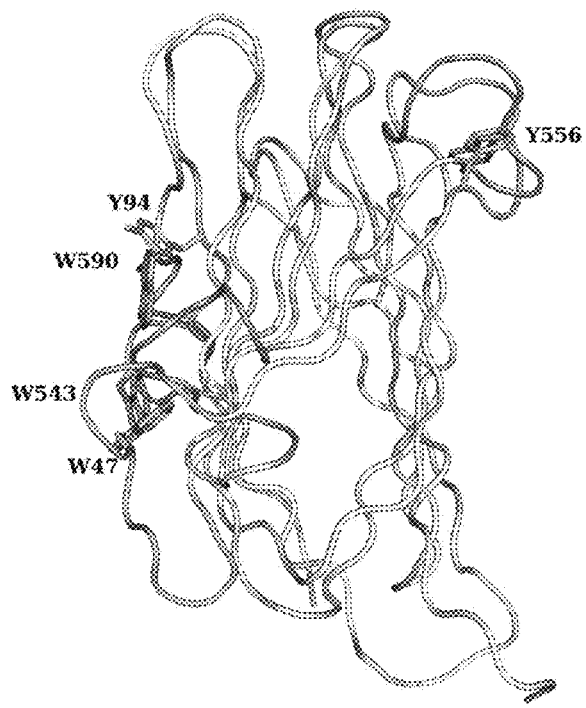
FIG. 3(A) shows structural superimposition of RoGACBM21 (PDB code: 2v81) and AnGACBM20 (PDB code: 1ac0) complexes. Three main structural differences, loops β34, β45, and β78, are shown. The key residues Trp47, Tyr94, and Phe58 in RoGACBM21 as well as the corresponding residues, W543, W590, and Y556, in AnGACBM20 are shown. In order to clearly examine the structural differences, the βCD molecules are not shown. (B) shows structural superimposition for binding site I of RoGACBM21 and AnGACBM20 complexes. Residues Trp47, Tyr83, and Tyr94 of RoGACBM21 and the corresponding residues in AnGACBM20, Trp543 and Trp590, are shown in sticks. (C) shows structural superimposition for binding site II of RoGACBM21 and AnGACBM20 complexes. Residues Tyr32 and Phe58 of RoGACBM21; the corresponding residues in AnGACBM20, Tyr527 and Tyr556, are shown in sticks.
Figure 3:
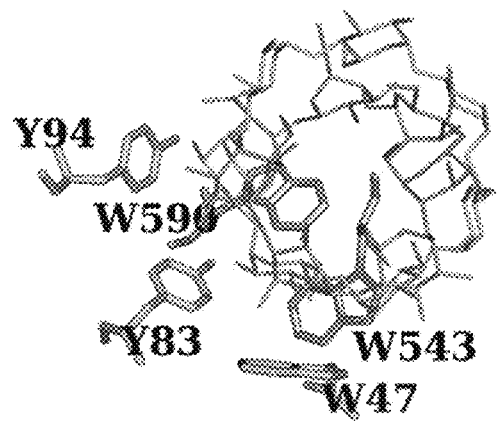
Figure 3:
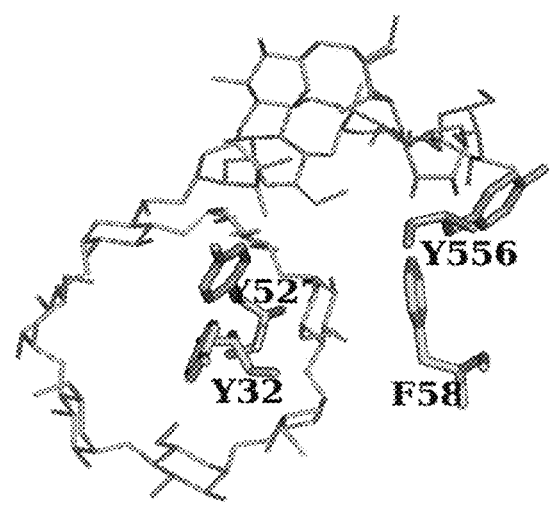
Figure 4:
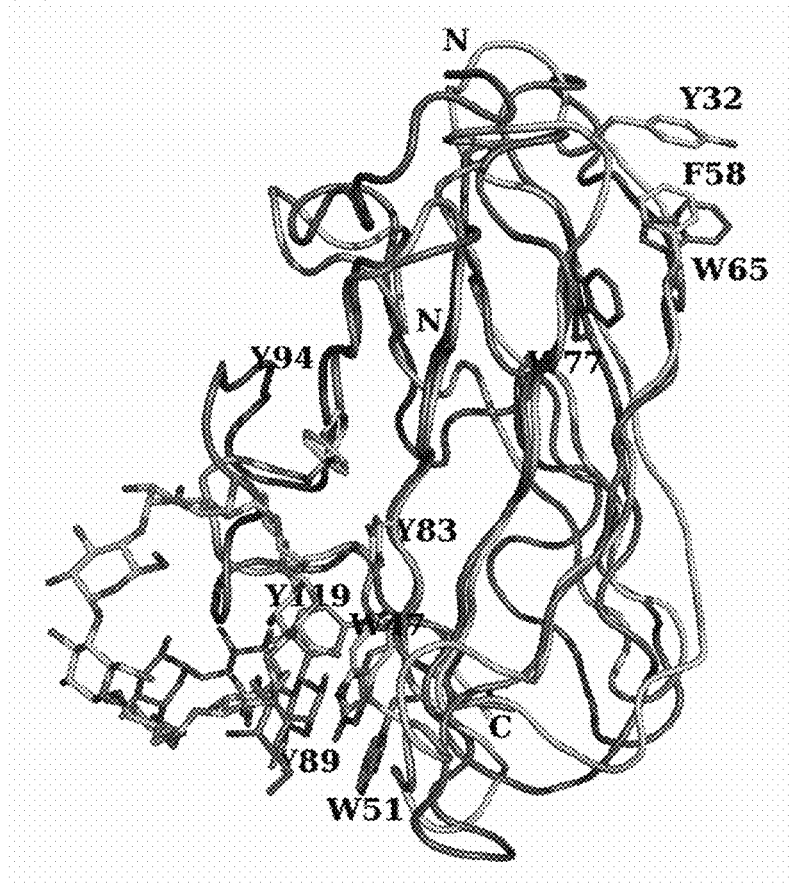
FIG. 4(A) shows structural superimposition of RoGACBM21 (PDB code: 2v81) and TvAICBM34 (PDB code: 1uh3) complexes. (B) Structural superimposition for binding site I of RoGACBM21, BhCBM25 (PDB code: 2c3x), and TvAICBM34 complexes. Residues Trp47, Tyr83, and Tyr94 of RoGACBM21 and the corresponding residues, Trp51, and Tyr89, and Tyr119 in TvAICBM34 as well as His26, Trp34, and Trp74 in BhCBM25 are shown in sticks. The ligands, βCD, maltotetraose, and transglycosylated acarbose for RoGACBM21, BhCBM25, and TvAICBM34, respectively, also are shown in sticks.
Figure 4:
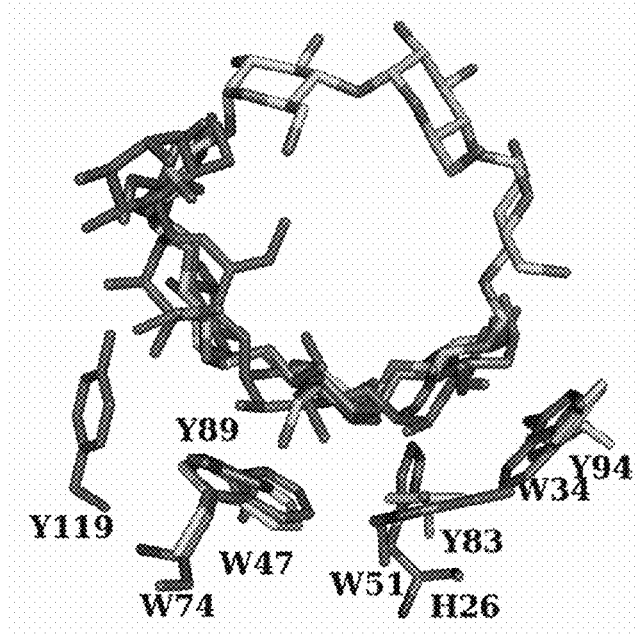

The superimposed images of liganded SBDs, SBD-βCD and SBD-G7 complexes, and unliganded SBD (PDB code: 2djm) were presented in FIG. 2. Essentially, both SBD-βCD and SBD-G7 complexes exhibited very similar overall structures. The residues involved in sugar binding and the hydrophobic and ring stacking interactions were well conserved in these two complexes. RoGACBM21 could adopt different sugar molecules, which helped keep the protein in a fixed conformation upon binding. These results indicated that the sugar binding site of SBD was rather fixed and stable. As long as the β-barrel scaffold was formed and the three key binding positions, Trp47, Tyr83, and Tyr94 could be preserved, the sugar binding would take place. The binding assay results for βCD and G7 complexes had been reported, with $K_d$ values of about 5 μM. The $K_d$ for the complex of linear and shorter sugar substrates, such as maltotriose and maltotetraose, were only about half of that for βCD and G7 complexes. Also, the $K_d$ (~333 μM) of the βCD complex was much higher than that of βCD and G7 complexes because the cyclic ring of the six glucose units of αCD was too small to fit the essential binding surface of SBD, such that its binding ability dramatically reduced.

The unliganded and liganded SBDs revealed similar overall structures with an RMSD value of 1.02 Å in Cα for the SBD-βCD complex and 0.97-1.09 Å for four molecules in the SBD-G7 complex. Three major structural differences, Trp47 (around loop β34), Glu68 (around loop β45), and Asn101 (around loop β78), were observed (FIG. 2A). Comparisons of the residues involved in direct hydrophobic and hydrophilic interactions were shown in FIGS. 2B and 2C. These interactions revealed a larger conformational change in site I around loop β34 upon sugar binding, especially for residues Trp47, Asn50, and Asn101, in which the main chains were present in different orientations. For the key aromatic residues in site I, the indole ring of Trp47 of liganded SBDs was rearranged to form the hydrophobic interaction with sugar ring of the carbohydrate molecule; however Tyr83 and Tyr94 did not show many structural differences. For site II, Tyr32 residues were in a similar orientation, but the phenyl ring of Phe58 of liganded SBD inverted to make the interaction with the glucose (FIG. 2B). In the liganded SBDs, Asn50 was flipped over to provide a strong hydrogen bond with βCD (NH2-O6:2.7 Å), and Asn29 revealed a different orientation to promote a hydrogen bond with βCD (NH2-O3:2.8 Å) (FIG. 2C).

Comparison of RoGACBM21 Complexes with Other Starch Binding Domains of CBM Superfamilies AnGA shared the same glycoside hydrolase characteristic as RoGA. However, the SBD of both proteins, AnGACBM20 and RoGACBM21, folded with different topologies (J. Y. Tung, M. D. Chang, W. I. Chou, Y. Y. Liu, Y. H. Yeh, F. Y. Chang, S. C. Lin, Z. L. Qiu, Y. J. Sun, Crystal structures of starch binding domain from *Rhizopus oryzae* glucoamylase reveal a polysaccharide binding path, Biochem J, 416 (2008) 27-36) and linked with catalytic domains through its N-terminal and C-terminal ends, respectively. The three dimensional structures of two SBDs could be superimposed by switching the first and the last strands (FIG. 3A) and the structural superimposition was presented in FIG. 3. Most CBM superfamilies contained one sugar binding site; however, RoGACBM21 and AnGACBM20 complexes each contained two binding sites. RoGACBM21 bound cooperatively to sugar, whereas AnGACBM20 exhibited independent sugar binding. Even though the sugar binding location was similar between both proteins, several structural differences were noted (FIG. 3A), especially loops β34, β45, and β78 around the sugar binding regions, which were in completely different conformations. These distinct loops provided the unique sugar binding for RoGACBM21 and AnGACBM20.

Two binding sites of both proteins were structurally and functionally different and the corresponding residues for site I and site II in AnGACBM20 were Trp543 and Trp590 (FIG. 3B) as well as Tyr527 and Tyr556 (FIG. 3C). In AnGACBM20, site I (W543) acted as the initial recognition site for starch, whereas site II (Y527) was capable of recognizing a range of orientations for starch strands. Site I had a larger surface area, underwent a conformational change upon sugar binding, and acted as a more specific site to lock the ligand into place. However, the structural and functional assay data for the RoGACBM21 complexes showed that site I (Trp47) was the essential binding site and site II (Tyr32) played an auxiliary role in carbohydrate binding. The corresponding residues to Trp47 in most SBD superfamilies were highly conserved except BhCBM26. Site I revealed a larger and broader binding surface, and underwent further conformational changes upon βCD binding.

TvAI showed different hydrolase characteristics with RoGA. However, RoGACBM21 and TvAICBM34 belonged to the N-terminal starch binding CBM superfamily and folded with the same type II topology (J. Y. Tung, M. D. Chang, W. I. Chou, Y. Y. Liu, Y. H. Yeh, F. Y. Chang, S. C. Lin, Z. L. Qiu, Y. J. Sun, Crystal structures of starch binding domain from *Rhizopus oryzae* glucoamylase reveal a polysaccharide binding path, Biochem J, 416 (2008) 27-36). Although the sequence identity and similarity of these two molecules were only 16 and 36%, respectively, their structures superimposed quite well, especially the β strands. The structural superimposition of RoGACBM21 and TvA-ICBM34 was shown in FIG. 4A with an RMSD of 1.6 Å in Cα. Nevertheless, several structural differences were still observed in loop regions, for example loops β34 and β78 (FIG. 4A). Two sugar binding sites of TvAICBM34 were in similar orientations to those of RoGACBM21 and two sugar molecules were in a perpendicular orientation. Meanwhile, the functional roles of two sugar binding sites in both proteins were comparable; site I/site-NA bound sugar specifically and site II/site-N helped the enzyme to approach starch by recognizing the starch surface.

The unique carbohydrate binding curvature was observed in most SBDs superfamilies, such as TvAICBM34, BhCBM25, and RoGACBM21. This binding platform, which provided the main protein-carbohydrate interactions, was formed by several key residues, for example: Trp47, Tyr83, and Tyr94 in RoGACBM21, Trp51, Tyr89, and Tyr119 in TvAICBM34 as well as His26, Trp34, and Trp74 in BhCBM25 (FIG. 4B). These key residues had a similar location, and their aromatic rings held the sugar molecules by hydrophobic stacking interactions (FIG. 4B). The most conserved residues among them were Trp47 in RoGACBM21, Trp74 in BhCBM25, and Tyr89 in TvAICBM34. This binding curvature could swing around the substrate to create a tight binding pocket and induced at least three glucose units of sugar molecules to be bent as a segmental shape for binding.

To go along with the different catalytic functions in these CBMs, the divergence of binding site II would be corresponding to recognize different linkages of the amylose chain such as α-1,4 and/or α-1,6 linkages. The distinct binding site II produced by Tyr32 and Phe58 of RoGACBM21 complexes (FIG. 1A) was not observed in SBDs from other CBM families (families 20, 21, 25, 26, 34, 41, 45, and 48), which functioned in recognizing the branch amylose.

Binding Affinity for Starch and βCD

To elucidate the mechanism of polysaccharide binding, the essential residues in the vicinity of the binding sites according to the complex structures had been examined. A number of RoGACBM21 mutants were generated and characterized by quantitative binding isotherm and fluorescence spectroscopic analysis (Table 2). The mutant proteins included the aromatic residues from site I (W47A, Y83A, and Y94A) and site II (Y32A and F58A) which were involved in βCD and G7 binding, and two additional tyrosine residues near sites I and II, Y67A and Y93A. The mutants of hydrophilic residues from site I (N50A, N96A, and N101A) and site II (N29A, K34A, and E68A) involved in direct hydrogen bond interactions with ligands were also analyzed.

The site I mutants (W47A, Y83A, and Y94A) exhibited decreased binding affinity for starch and βCD as compared with the $K_d$ values for wild-type RoGACBM21 (Table 2). The W47A mutant was devoid of binding affinity for βCD. Meanwhile, W47A, Y83A, and Y94A showed a reduced $B_{max}$ for binding capacity to starch, especially Y83A, with the lowest $B_{max}$, because Tyr83 was located on the inside position of the site I binding curvature. The site I (W47A) would serve as the major carbohydrate binding site for starch. For the site II mutants (Y32A and F58A), the $K_d$ values of Y32A for starch and βCD binding were similar to that of wild-type SBD. In addition, Y32A had less effect in the binding of soluble oligosaccharides. F58A showed an increased $K_d$ for the binding of starch and the highest $K_d$ for the binding of βCD among all mutants; however, it revealed almost no effect in the binding capacity for starch with a similar $B_{max}$ to that of wild-type SBD. Since Phe58 showed significant effect in the binding to βCD and starch, the Phe58 would play a key role in site II.

Although Tyr67 and Tyr93 did not directly interact with βCD and G7 in the SBD-βCD and SBD-G7 complexes (FIG. 1), Y67A and Y93A mutants revealed apparently lower $B_{max}$ and higher $K_d$ values (Table 2). In particular, Y67A had a considerably reduced $B_{max}$ (3.7 μmole/g), the lowest starch binding capacity of all the mutants. Interestingly, structure-based alignment indicated that the corresponding position of Tyr67 in most of SBD containing CBM superfamilies was an aromatic residue and Tyr93 was also conserved in most of the CBM21 superfamily (J. Y. Tung, M. D. Chang, W. I. Chou, Y. Y. Liu, Y. H. Yeh, F. Y. Chang, S. C. Lin, Z. L. Qiu, Y. J. Sun, Crystal structures of starch binding domain from *Rhizopus oryzae* glucoamylase reveal a polysaccharide binding path, Biochem J, 416 (2008) 27-36). The present invention demonstrated that Tyr67 played an important role in governing the starch binding capacity for RoGACBM21.

Table 2 presented $K_d$ and $B_{max}$ values for hydrophilic residue mutants from site I (N50A, N96A, and N101A) and site II (N29A, K34A, and E68A). Mutant N50A had a reduced $B_{max}$ and the highest $K_d$ (~10 folds) for starch binding among all site I and II mutants. The $B_{max}$ and $K_d$ values for N50A were attributable to the loss of hydrogen bond interactions between Asn50 and Tyr83. These data indicated that Asn50 must play a major role in the binding of insoluble polysaccharides and contribute to the integrity of site I. Mutants N96A and N101A (site I) as well as K34A and E68A (site II) had inefficient binding of βCD, with high $K_d$ values due to a loss of hydrogen bond interactions. Consequently, these hydrophilic residues from sites I and II would play a critical role in the binding of soluble or insoluble polysaccharides, in either an individual or cooperative manner.

TABLE 2

Binding affinity of wild-type and mutant RoSBD for starch and β-cyclodextrin

| Protein | Starch | | β-cyclodextrin |
|---|---|---|---|
| | $B_{max}$ (μmol/g) | $K_d$ (μM) | $K_d$ (μM) |
| WT | 41.1 ± 1.1 | 1.4 ± 0.1 | 5.1 ± 0.7 |
| Mutants of aromatic residues | | | |
| Y32A | 23.1 ± 0.6 | 2.5 ± 0.3 | 17.8 ± 1.4 |
| W47A | 21.9 ± 1.0 | 7.8 ± 1.1 | |
| F58A | 37.5 ± 1.4 | 4.6 ± 0.5 | 28.4 ± 3.5 |
| Y67A | 3.7 ± 0.1 | 6.5 ± 0.4 | 10.2 ± 1.4 |
| Y83A | 6.4 ± 0.1 | 7.1 ± 0.4 | 15.4 ± 2.7 |
| Y93A | 27.8 ± 0.2 | 2.7 ± 0.1 | 14.9 ± 1.4 |
| Y94A | 27.0 ± 1.1 | 3.5 ± 0.5 | 12.7 ± 1.4 |
| Mutants of hydrophilic residues | | | |
| N29A | 7.0 ± 0.2 | 8.1 ± 0.6 | 6.5 ± 0.9 |
| K34A | 7.7 ± 0.1 | 5.2 ± 0.4 | 22.5 ± 2.5 |
| N50A | 4.5 ± 0.1 | 13.6 ± 1.1 | 7.7 ± 0.9 |
| E68A | 6.5 ± 0.1 | 6.8 ± 0.2 | 22.0 ± 3.0 |
| N96A | 24.0 ± 0.3 | 1.6 ± 0.1 | 23.4 ± 3.0 |
| N101A | 17.8 ± 0.4 | 2.9 ± 0.2 | 25.2 ± 3.3 |

A Novel Amylosic Polysaccharide-SBD Binding Model

Figure 5A:
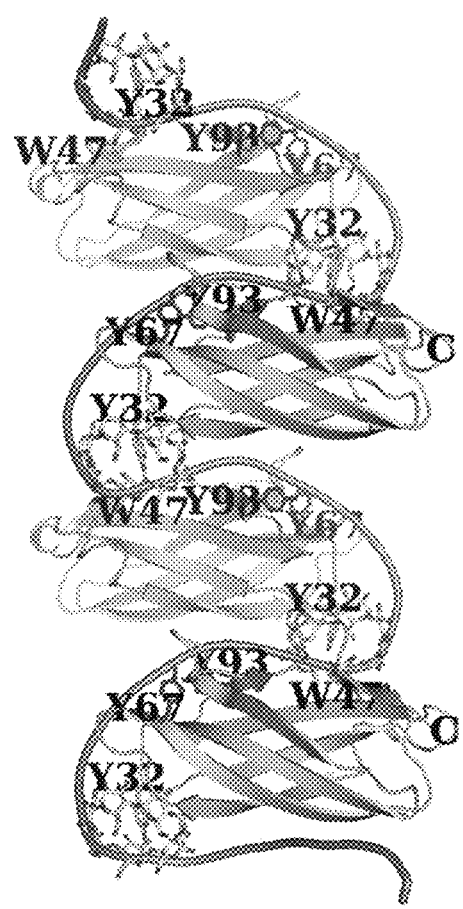
FIG. 5(A) shows the amylosic polysaccharide-SBD binding model in stereo view. The sugar molecules, βCD of RoGACBM21 are shown in sticks. Residues, Trp47 (site I), Tyr93, Tyr67, and Tyr32 (site II) involved in the polysaccharide binding are shown in sticks. The C-terminuses of RoGACBM21 are labeled. (B) Ultra-structure of amylose in the presence of RoSBD. The AFM images of the structure were obtained after incubating amylose solution with solution at room temperature for 16 hr. [Amylose]:[protein]: (a) 25 ng/mL:30.55 µM; (b) 0.25 µg/mL:30.55 µM; (c) 2.5 µg/mL:30.55 µM; (d) 2.5 µg/mL:3.06 µM; (e) 2.5 µg/mL:0.31 µM; (f) 2.5 µg/mL:31 nM; scan sizes 5 µm×5 µm. Scale bar was 1 µm. (C) The model of amylose disruption by RoSBD of the present invention. Step 1: Approach. RoSBDs approach amylose aggregates; Step 2: Binding. RoSBDs bind to amylose; Step 3: Loosening. RoSBDs loosen amylose aggregates to expose more surface for RoSBD binding; Step 4: Unwinding. RoSBDs unwind the amylase aggregates to smaller fibers; Step 5: Spreading out. RoSBDs finally turn fibers into single amylose molecules and spread them out.
Figure 5B:
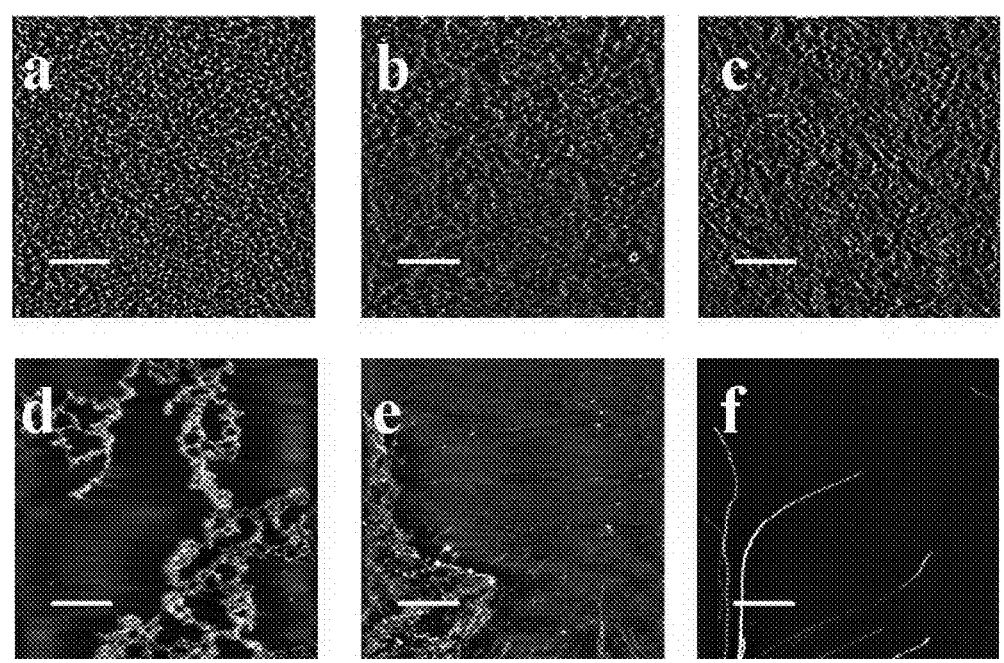

In RoGACBM21 complexes, two carbohydrate binding sites I and II could be connected through 11 amino acids on the surface of SBD by auxiliary residues, Tyr67 and Tyr93. Residues Tyr67 (loop β4-5) and Tyr93 (loop β6-7) acted as a midpoint to link two binding sites and made a continuous binding patch for longer chain and larger polysaccharides, or even starch. The distance of this potential starch binding patch through Trp47 (site I), Tyr93, Tyr67, and Tyr32 (site II) was in a range of 45-60 Å with a surface area of about 1,215 Å2. Comparing the two strong and specific binding sites, I and II, the continuous binding around Tyr67 and Tyr93 was particularly important for the raw starch/insoluble polysaccharides, but not for soluble and smaller carbohydrate molecules, such as βCD and G7. During the initial binding step, sites I and II acted as two persistent binding markers for soluble/insoluble polysaccharides, after which the continuous binding patch will assist further binding. A novel amylosic polysaccharide-SBD binding model was generated from the molecular packing of the SBD-βCD complex (FIG. 5), four SBD molecules aligned and packed as a helix along the vertical axis and the continuous ligand binding surface was constituted by βCDs to mimic the natural helical structure of amylose. Furthermore, although only the N-terminal domain (SBD) of RoGA was shown in the amylosic binding model; the C-terminal catalytic domain of RoGA appeared to be bound through a flexible linker on two sides interlacing each other along this helical arrangement. RoGACBM21 was superimposed with the TvAICBM34 domain of the TvAI to imitate the full-length RoGA (data not shown). This tentative full length RoGA applied in the amylosic binding model clearly demonstrated that the C-terminal catalytic domain was located in a reasonable orientation and did not block the polysaccharide binding of SBD. A similar binding model between the amylose chains and SBDs was suggested in AnGACBM20 using atomic force microscopy (AFM) images. The ring-like structure was proposed, in which parallel strands of the amylose molecule bound to both binding sites of SBD and the SBDs formed a template for the assembly of an expanded amylosic double helix. The interaction between amylose and the RoGACBM21 was also measured using AFM (FIG. 5B). When RoGACBM21 was incubated with the amylose, the appearance of deposited amylose changed dramatically. According to AFM analysis results, an amylose disruption model was proposed as shown in FIG. 5C. First, RoSBDs approach amylose aggregates and then bind to the end of amylose chains. Upon binding to amylose, RoSBDs loosen amylose aggregates to expose more polysaccharide surface for RoSBD binding. As a result, the amylose aggregates would be unwound to form smaller fibers and finally spread out and turned into smaller amylose units as a single amylose chain. The giant filamentous amylose was diminished by RoGACBM21 gradually and the donut ring shape RoGACBM21 complexes were formed. Moreover, the working model of the present invention provided a rationale to account for the appearance of tandem repeat of SBDs in some cases, for example BhCBM26/CBM25 tandem and CBM41s tandem molecules of pullulanases from *Streptococcus*. In which low affinity was observed between single SBD unit and polysaccharides, whereas much higher ligand binding affinity could be obtained with multiple SBD units. Taken together, the present invention had shed a light in construction the molecular model for an interaction between CBMs and long chain polysaccharides. The application based on this model is including producing an oligosaccharide of desired length by changing the linker or the catalytic domain of SBD, or quantitating a polysaccharide by a SBD linked to a fluorescent material.

Example 2

Preparation of Recombinant SBDs
In the present invention, several wild-type and mutant SBD clones, including SBD (SEQ ID NO:1), SBD (ΔK108) (SEQ ID NO:2), SBD (K108A) (SEQ ID NO:3), SBD (K108R) (SEQ ID NO:4), SBD (K108H) (SEQ ID NO:5), and SBD (K108D) (SEQ ID NO:6) were constructed and expressed in *Escherichia coli* BL21 Gold (DE3) cells using pET-32a (+) as the expression vector. Protein expression and purification were carried out as described previously. Protein concentration was determined with the BCA Protein Assay Kit (Pierce) and the starch binding analysis was performed as described previously.

Circular Dichroism (CD) Spectroscopy and Thermal Stability
CD spectra and thermostabilities were recorded in a 0.1-cm cuvette using an Aviv model 202 CD Spectrometer. Data collection and calculation were carried out as previously described.

Saturation Binding Assay
To analyze the saturation binding ability, 100 µL of purified SBD (5 to 90 µM) were each mixed with 1 mg of pre-washed corn starch (Sigma-Aldrich) and incubated at 25° C. for 3 h before being centrifuged at 13,000×g for 10 min. After centrifugation, the non-bound protein concentration was determined using the Micro BCA protein assay reagent kit (Pierce). Then, the amount of adsorbed protein was calculated by subtracting the final protein concentrations from the initial concentrations.

Peptide Design and Synthesis
The synthetic peptide CT-14 (SEQ ID NO:7) corresponding to the last fourteen C-terminal residues of SBD and its variants with alanine substitutions for each residues (SEQ ID NO:11-27 ) were obtained commercially (Bio-Synthesis Inc.). The purity of the peptides was greater than 90%.

Congo Red Assay for Fibril Formation
The Congo Red solution was made fresh and filtered through a 0.2-µm filter prior to use. After incubation at 37° C. for 72 h, the protein solution (100 µg/mL) was stained with Congo red (50 µM) and examined by measuring the absorption in the wavelength range of 400-600 nm using a UV spectrophotometer.

Thioflavin T Fluorescence (ThT) Assay for Fibril Formation
Purified SBDs or synthetic peptides were dissolved in 10 mM sodium-citrate or phosphate-citrate buffer to a final concentration of 100 µM (at indicated pH). Two hundred microliters dissolved proteins were incubated with 10 µM of ThT solution in a volume of 2 mL at 37° C. for 10 min to demonstrate the formation of β-amyloid-like fibrils. The measurements were recorded in a Perkin Elmer LS-55 spectrofluorometer at 25° C.

The relative fluorescence, peaked at 482 nm, subtracted from the background of buffer from the total fluorescence were measured as the amount of fibrillar aggregates with the excitation wavelength (slit width=4 nm) set at 450 nm and monitoring emission wavelength (slit width=8 nm) set at from 470 to 630 nm.

Transmission Electron Microscopy (TEM)
Coated copper grids were placed onto sample drops containing the heat-induced amyloid-like fibrils of SBD for 10 min. The samples were washed to remove excess solution, stained with 1% (w/v) uranyl acetate for 1 min and the grids were then air-dried before being analyzed by Hitachi H-7500 TEM as described.

Ultracentrifugation
The sedimentation velocity studies were performed at 50,000 rpm for 30 µM (solid line) and 60 µM (dotted line) SBD, and absorbance scans were recorded at 280 nm.

Atomic Force Microscopy (AFM)
The wild-type and mutant CT-14 peptides were individually incubated in 10 mM sodium citrate buffer (pH 4.5) to a final concentration of 100 µM at 37° C. for 0, 6, 12, 24, 48 and 72 h. Fifty microliters of sample solution (25 µM) was spotted onto freshly cleaved mica. After an adsorption period of 10 min on the surface, the solution was washed with tenfold-volume of ddH$_2$O and air-dried. The fibrillar images were obtained using a Nanowizard AFM system (JPK instruments, Germany) operated in contact mode with a silicon nitride cantilever (BudgetSensors, Bulgaria).

Solid-state NMR Spectroscopy

The NMR spectra were collected at 7.04 Tesla corresponding to a $^{13}$C Larmor frequency of 75.47 MHz on a Bruker (Rheinstetten, Germany) Avance 300 NMR spectrometer equipped with a Bruker double-resonance MAS probe with a 4.0-mm zirconium oxide MAS rotor. For the $^{13}$C-CP/MAS experiments, the cross-polarization contact time was 1.0 ms while the $^1$H decoupling field strength was 87.8 kHz, and a proton 90° pulse width of 3.5 µs was used at rf amplitudes of 71.4 kHz. During the acquisition period, $^1$H TPPM decoupling sequence was applied at the rf amplitudes of 79 kHz. A recycle delay of 5 s was used. All MAS experiments were collected at ambient temperature with the sample spinning at 8.0 kHz regulated by the spinning controller within ±1 Hz.

Heat-Induced Conformational Changes in SBDs

Figure 6:
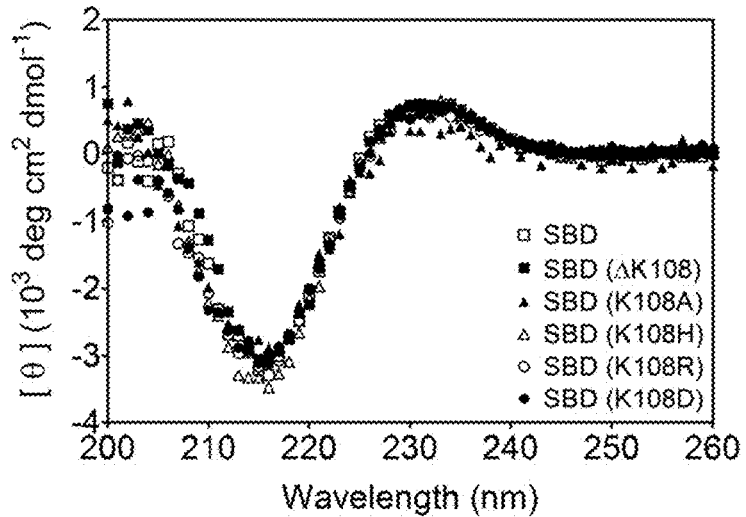
FIG. 6 shows the heat-induced secondary structure and conformational changes of SBD. (A) CD spectra were collected from 200 to 260 nm at 25° C. at a concentration of 50 µM in 10 mM sodium acetate buffer (pH 4.5). (B) Thermal unfolding of SBD was measured by monitoring changes in the far-UV CD spectra at 215 nm. (C) CD spectra of SBD were recorded between 200 and 260 nm at various temperatures
Figure 6:
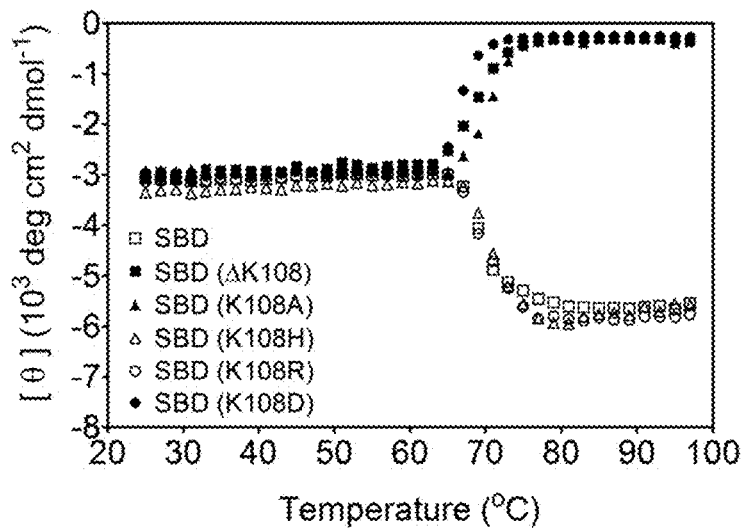
Figure 6:
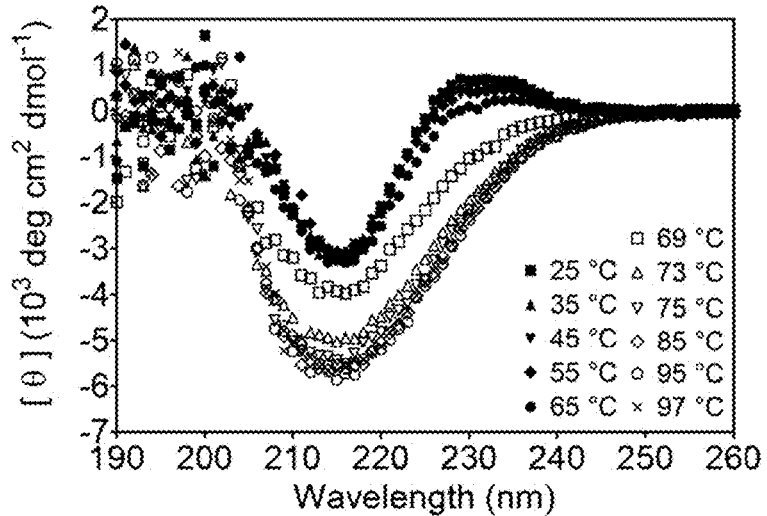
Figure 7:
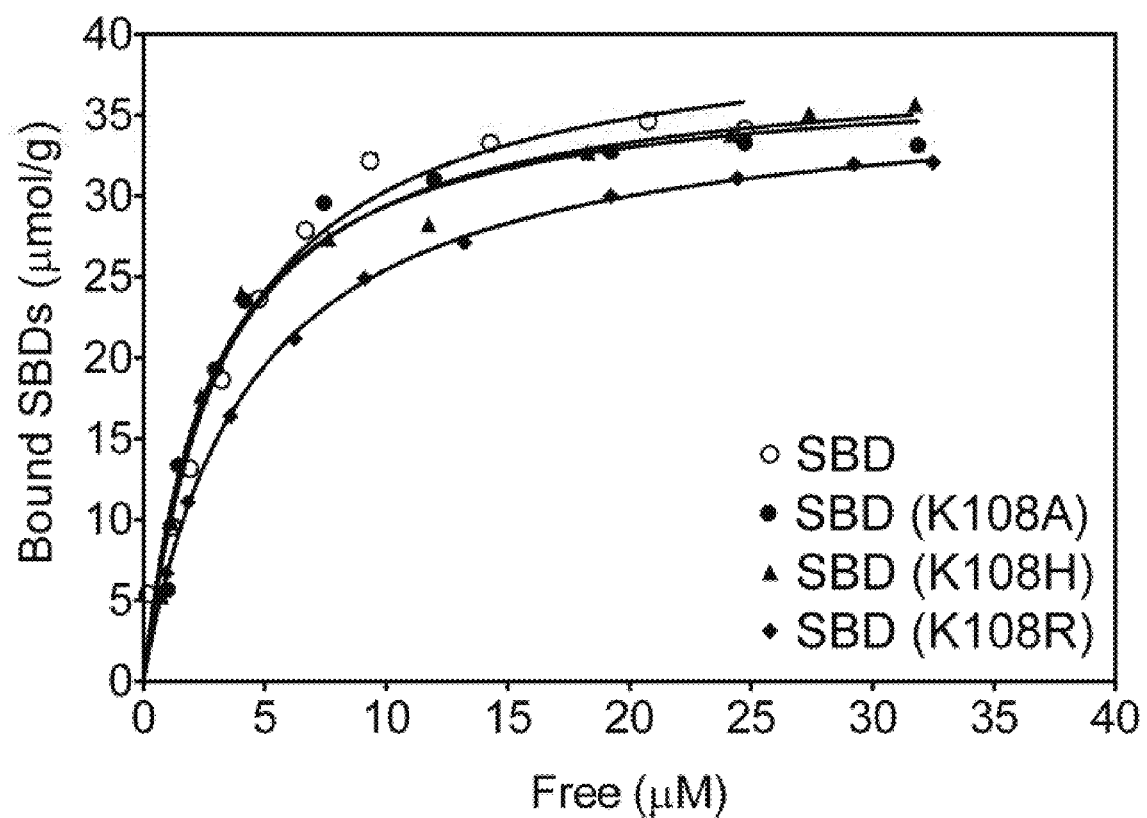
FIG. 7 shows the ligand binding affinity of recombinant SBD variants. The recombinant proteins were individually co-incubated with corn-starch at 25° C. for 3 hr, centrifuged at 13,000×g for 10 min, and binding isotherms for starch were fitted.

The SBD from *R. oryzae* GA consisted of eight β-strands according to its three-dimensional structure. As expected, the far-UV CD spectrum displayed a trough at 215 nm, a characteristic of β-strand conformation (FIG. 6A). In this context, thermal unfolding of SBD using CD spectroscopy had been monitored. Thermal denaturation of SBD monitored at 215 nm exhibited a cooperative transition with increasing temperature (FIG. 6B, open square). The apparent temperature for unfolding of SBD corresponded to approximately 65° C. Surprisingly, the signal became more negative along with ascending temperature, indicating the increase in β-sheet content. In addition, deletion or Ala substitution of the C-terminal amino acid Lys108 of SBD led to disappearance of the physical morphology. Interestingly, when Lys108 of SBD was individually replaced with the positively charged amino acid, His or Arg, SBD (K108H) and SBD (K108R) still showed strong β-sheet signals upon heating (FIG. 6B, open circle and open triangle). On the contrary, negative charge at position 108 in SBD (K108D) diminished the β-sheet signals upon heating (FIG. 6C, closed circle). This further supported the notion that the positive charge at the C-terminal end of SBD contributed significantly to the conformational change process. In addition, the signals in the CD spectra of SBD became stronger with increasing temperatures, demonstrated fibril formation accompanied with the ordered assembly of some part of the protein molecule (FIG. 6C). Moreover, amino acid replacements at Lys108 had no significant influence on ligand binding (FIG. 7), indicating that the structures and biological functions of these SBD variants still maintained under normal condition. Taken together, the positive charge at the C-terminal end of SBD was not involved in direct ligand binding, but was required for thermal induced fibril formation.

Characterization of Heat-Induced SBD Oligomerization

Figure 8:
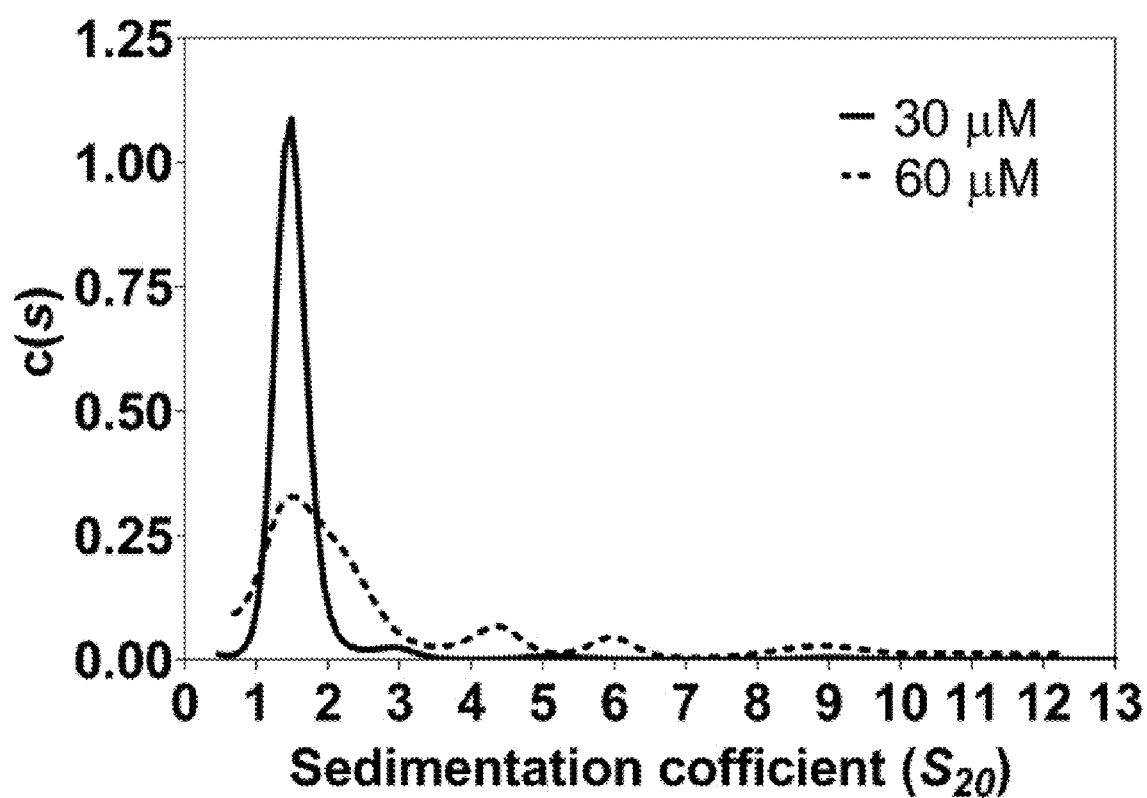
FIG. 8 shows the oligomerization of SBD by ultracentrifugation. The sedimentation velocity studies were performed at 50,000 rpm for 30 µM (solid line) and 60 µM (dotted line) SBD, and absorbance scans were recorded at 280 nm.
Figure 9:
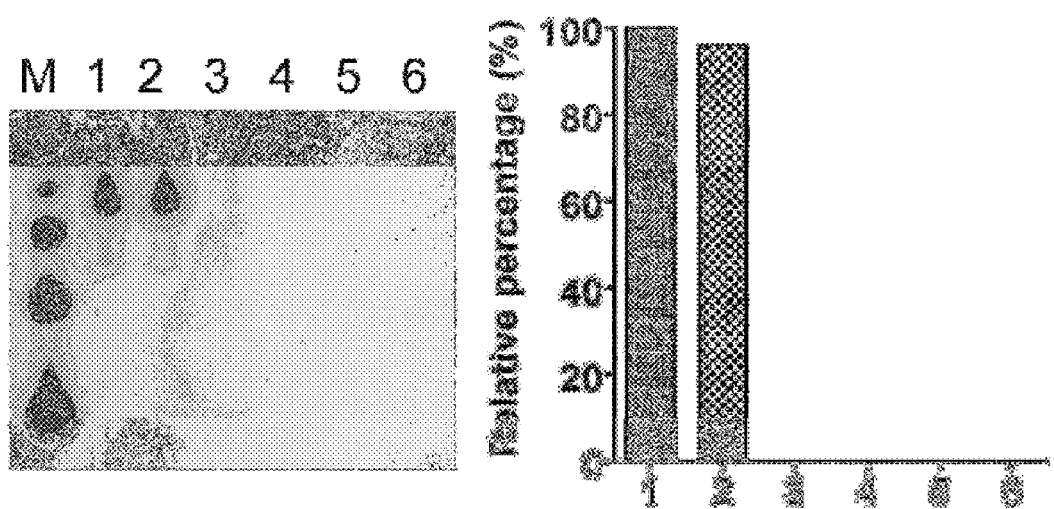
FIG. 9 shows effect of heating temperature and time on SBD oligomerization. (A) Effect of heating temperature on the oligomerization SBD. Fifteen microliters of SBD (0.85 mg/mL) were incubated for 5 min at different temperatures: 50° C. (lane 2), 60° C. (lane 3), 70° C. (lane 4), 80° C. (lane 5), 90° C. (lane 6). (B) Effect of heating time on the SBD oligomerization. SBD (0.85 mg/mL) incubated at 60° C. for different periods of time, 1 min (lane 2), 5 min (lane 3), 10 min (lane 4), 20 min (lane 5), 40 min (lane 6). To each lane of a native gel (8%), 15 µL of protein were loaded and lane M represents the BSA (20 µg) used as s positive control for native PAGE.
Figure 9:
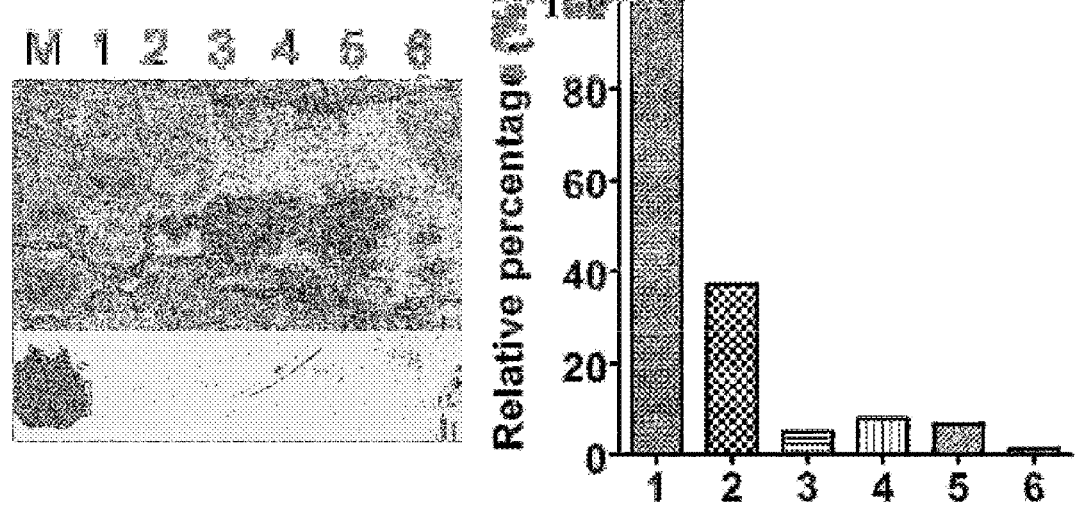

FIG. 8 showed a comparison of the continuous size distribution profiles of SBD at initial protein concentrations of 30 and 60 µM. At low concentration (30 µM) SBD presented mainly as a single monomeric species in solution, with an s$_{20}$ of 1.3 S and an apparent molar mass of 13,195 Da. Alternatively, at high concentration (60 µM) oligomeric forms of SBD appeared as evidenced by multiple signals of the sedimentation coefficient. Oligomerization of SBD could also be observed in native PAGE (FIG. 9). The oligomerization of SBD increased when the heating temperature was raised or when the heating time increased at a fixed temperature. The observation indicated that oligomerization behavior of SBD was concentration and temperature dependent.

Identification of Fibril Formation in SBD

Figure 10:
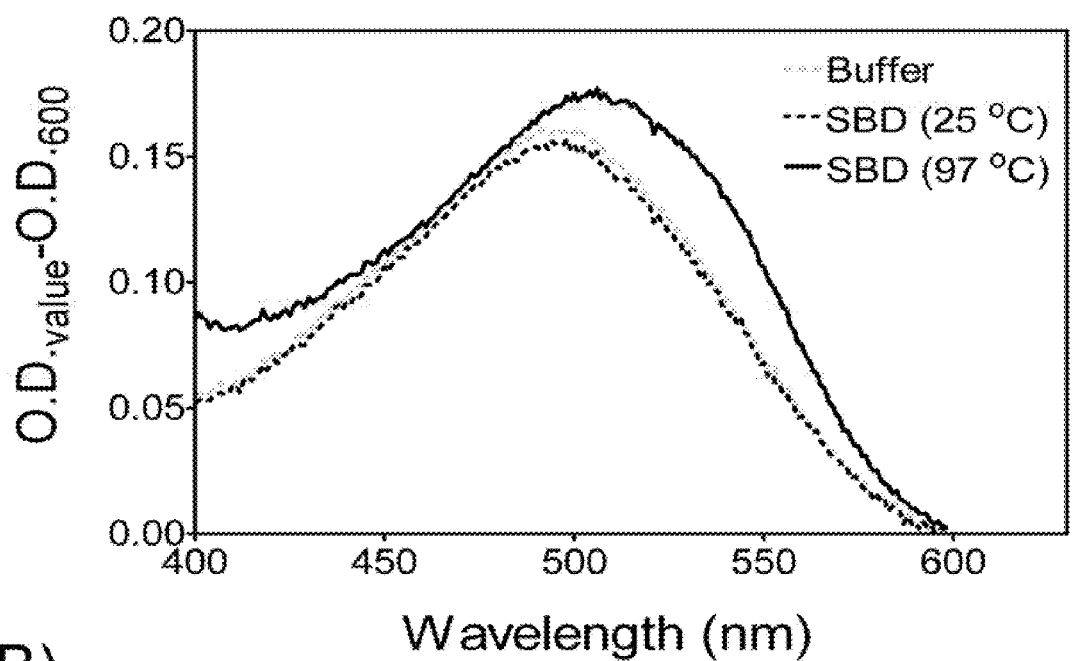
FIG. 10 shows the characterization of SBD fibril. (A) Absorption spectra after Congo Red binding to SBD samples with or without heat treatment. (B) Fluorescence emission spectrum of ThT in the presence of SBD samples with or without heat treatment.
Figure 10:
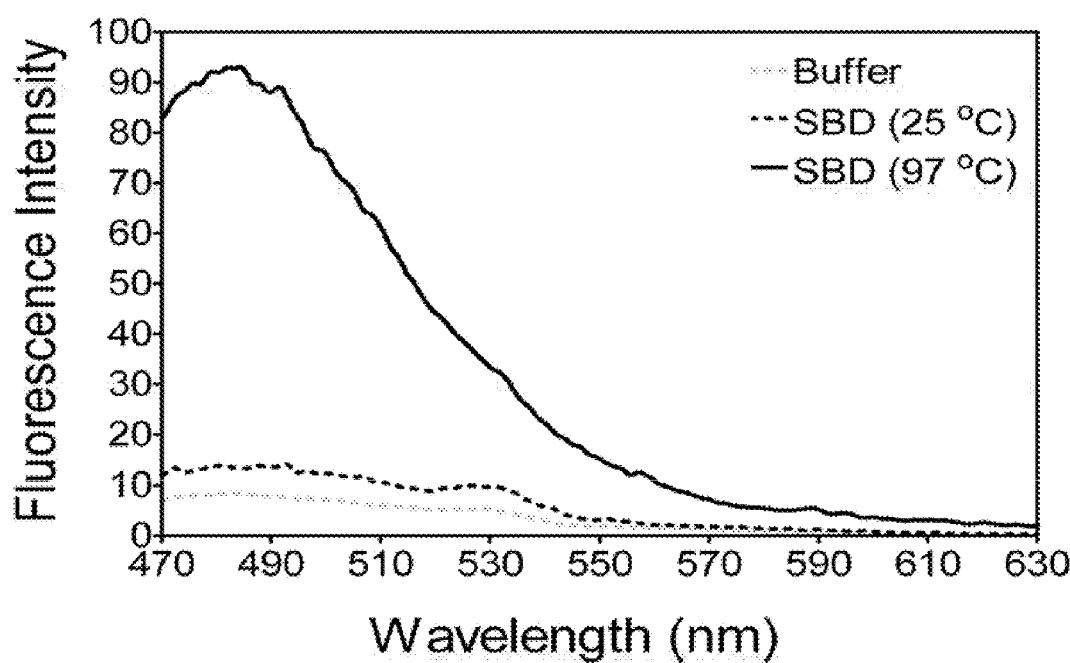

Congo Red was a useful dye to detect the formation of amyloid fibrils, and its binding assay was initially applied to examine if the structure of SBD formed at high temperature had characteristics of the amyloid-like fibrils. When the sample was heated at 97° C., the Congo Red absorption showed an evident red shift in the spectral maximum from 485-495 to 500-510 nm (FIG. 10A). In addition, ThT, a fluorescent dye for more sensitive detection of amyloid aggregation, was used as well. FIG. 10B depicted the changes in emission intensity of ThT. A 9-fold increase in the fluorescence emission intensity at 482 nm was observed in SBD sample heated at 97° C. SBD pretreated with heat bound both Congo Red and ThT, a common indication of presence of amyloid fibrils, demonstrating the formation of amyloid-like fibrils in the unique starch-binding CBM.

Characterization of the Fibril-forming SBD

Figure 11:
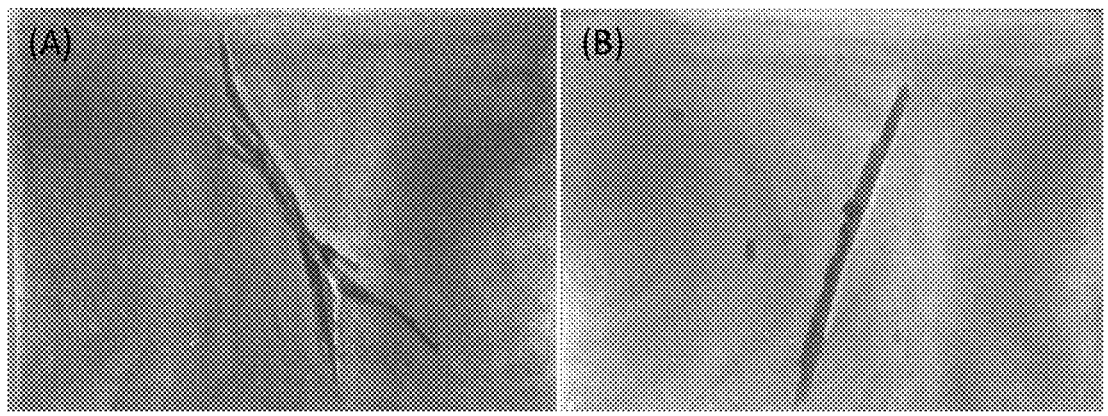
FIG. 11 shows the TEM images of SBD fibril in both (A) and (B). The SBD sample was heated to 97° C. and left to recover at 37° C. for 2 days, and then co-stained with uranyl acetate and observed by TEM.

When SBD was incubated at 37° C. for 2 days prior to examination by TEM whose images at 8,000-12000 folds magnification, formation of highly organized filamentous structures in SBD was evidently observed (FIG. 11). The average fibril diameter was about 10 to 20 µm. Thus, the SBD C-terminus conferred a β-amyloid-like fibril-forming capability to an SBD following heat treatment.

Identification of the Fibril-forming Segment in SBD

Figure 12:
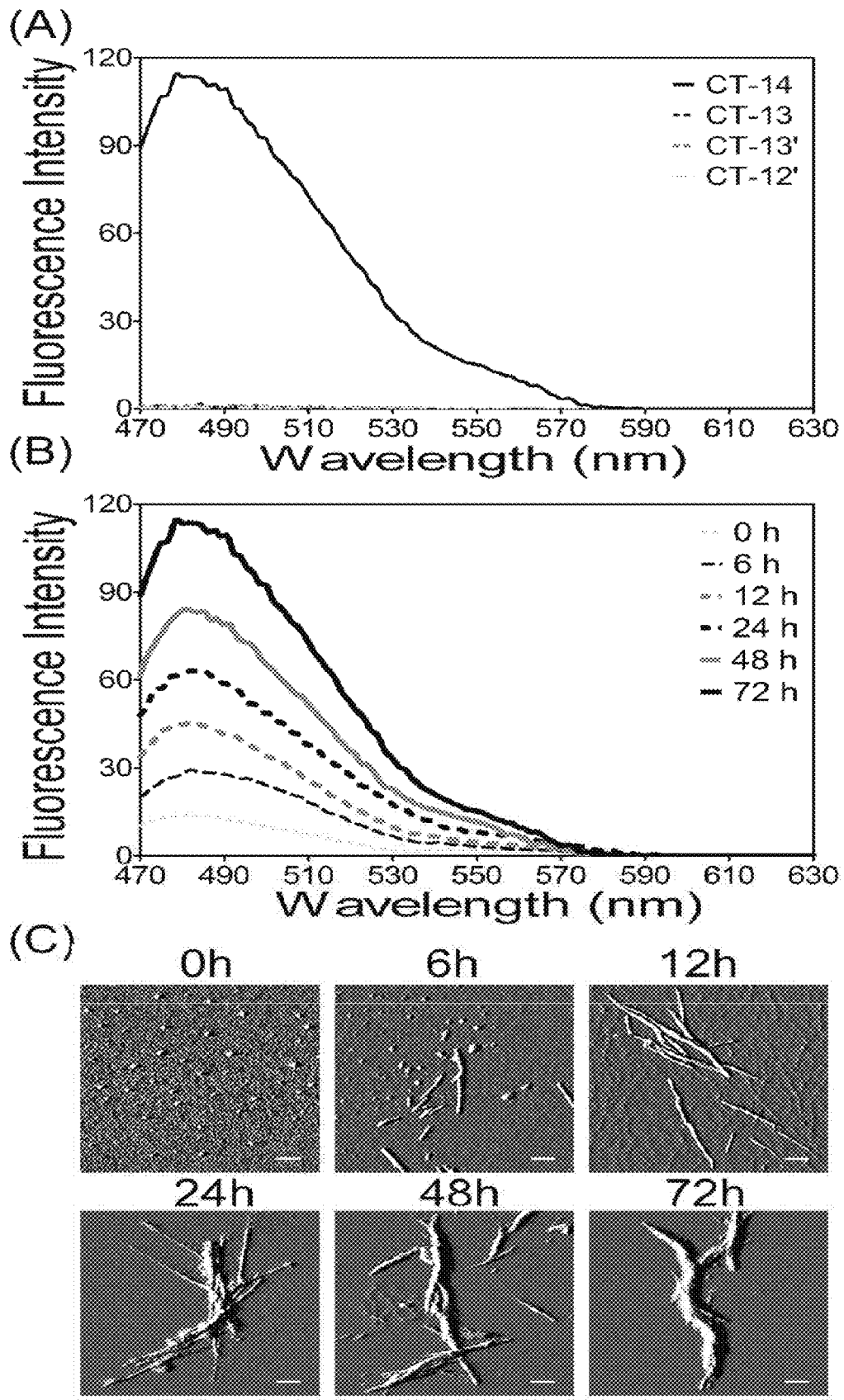
FIG. 12 shows the characterization of fibril formation in the CT-14 peptide. (A) ThT-binding analysis of CT-14, CT-13, CT-13' and CT-12' peptides. Fluorescence emission spectra of ThT, excited at 450 nm, were recorded between 470 and 630 nm. (B) CT-14 was incubated with ThT at 37° C. and fluorescence emission spectra were recorded. (C) The fibrillar CT-14 peptide obtained from (B) was deposited on freshly cleaved mica for the indicated time intervals and examined by AFM (scale bar=200 nm).

Abundant studies had indicated that some proteins' sub-regions, or short peptide segments, were crucial for the formation of amyloid-like fibrils. In addition, a variety of amyloidogenic peptides possessing aromatic-Asn or Asn-aromatic conjugates served as a common denominator for amyloid-like fibril formation. Given the Lys108 requirement which had been described, the C-terminal near-end portions of SBD including CT-14 (SEQ ID NO:7), CT-13 (SEQ ID NO:8), CT-13' (SEQ ID NO:9) and CT-12' (SEQ ID NO:10) were synthesized to identify the potential segment involving key steps in fibril formation (FIG. 12A). The fluorescence emission at 482 nm of ThT in the presence of CT-14 peptide pretreated at 37° C. formed amyloid-like fibrils, but under the same condition, CT-13, CT-13' and CT-12' were not ThT-positive (FIG. 12A, dashed curves); hence residues 95-108 of the SBD served as the minimal segment essential for fibril formation.

Ultrastructure of the Fibril-forming Peptide

The time-dependent ThT analyses of the present invention indicated a multi-step process in the fibril formation (FIG. 12B). The time-dependent morphological alteration of CT-14 fibrils was further examined by AFM (FIG. 12C). At 0 h, only spherical structures were observed while small protofibrils started to form after incubation at 37° C. for 6 h. The protofibrils began to elongate to form mature fibrils with the length surpassing 200 nm at 12 h. Upon incubation for 24 h, fibril aggregation occurred along with an elongation step. This phenomenon was more obvious at 48 and 72 h, consistent with the increased ThT signal at 482 nm (FIG. 12B). The segment of residues 95-108 of SBD could thus be defined as a sub-region capable of initiating the formation of fibrils.

Determination of Crucial Residues for CT-14 Fibril Formation

Figure 13:
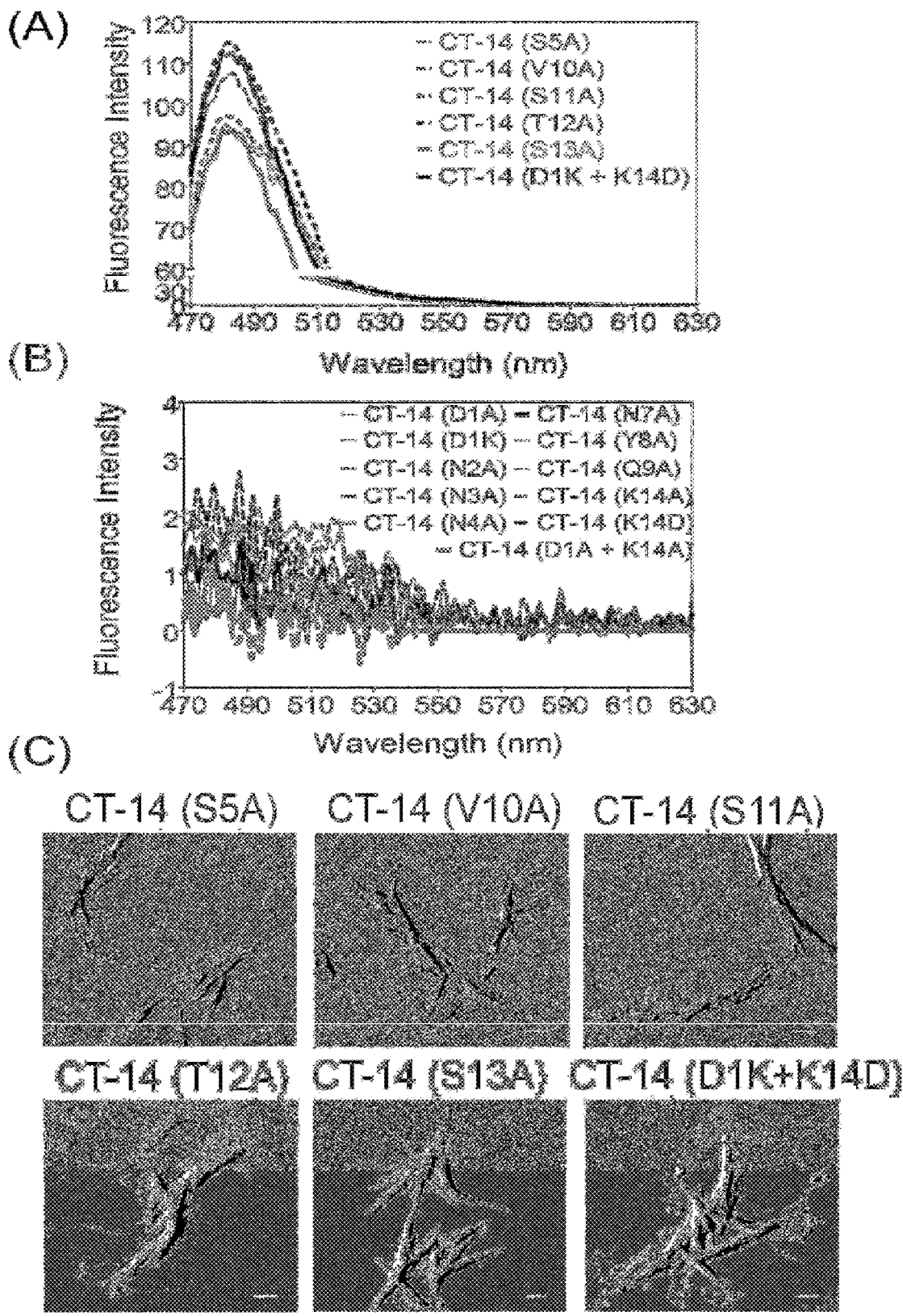
FIG. 13 shows the characterization of fibril formation in the CT-14 peptide. (A) Six CT-14 peptide mutants (S5A, V10A, S11A, T12A, S13A, and D1K+K14D) were incubated with ThT at 37° C. for 72 h and fibril quantities were determined by ThT. (B) Eleven CT-14 variants (D1A, D1K, N2A, N3A, N4A, N7A, Y8A, Q9A, K14A, K14D and D1A +K14A) were separately incubated with ThT at 37° C. for 72 h and fluorescence emission spectra were recorded. (C) The fibrillar CT-14 peptide obtained from (A) was deposited on freshly cleaved mica for the indicated time intervals and examined by AFM (scale bar=200 nm).

To identify specific key residues in the CT-14 peptide that govern fibril formation, alanine scanning mutagenesis was performed using a set of synthetic CT-14 peptide analogs. The emission spectrum of ThT in the presence of CT-14 peptides (SEQ ID NO:7), CT-14 (S5A) (SEQ ID NO:16), CT-14 (V10A) (SEQ ID NO:20), CT-14 (S11A) (SEQ ID NO:21), CT-14 (T12A) (SEQ ID NO:22), CT-14 (S13A) (SEQ ID NO:23), and CT-14 (D1K+K14D) (SEQ ID NO:27) showed an increase in fluorescence intensity at 482 nm similar to the wild type CT-14 peptide (FIG. 13A), whereas none of the other CT-14 variants, CT-14 (D1A) (SEQ ID NO:12), CT-14 (D1K) (SEQ ID NO:11), CT-14 (N2A) (SEQ ID NO:13), CT-14 (N3A) (SEQ ID NO:14), CT-14 (N4A) (SEQ ID NO:15), CT-14 (N7A) (SEQ ID NO:17), CT-14 (Y8A) (SEQ ID NO:18), CT-14 (Q9A) (SEQ ID NO:19), CT-14 (K14A) (SEQ ID NO:24), CT-14 (K14D) (SEQ ID NO:25) and CT-14 (D1A+K14A) (SEQ ID NO:26), could form fibrils (FIG. 13B). These data were consistent with the fibril-like structures detected by AFM analysis (FIG. 13C). This finding indicated that Ser5, Val10, Ser10, Thr12, and Ser13 in the CT-14 peptide did not contribute to fibril formation. On the other hand, both terminally charged residues (Asp1 and Lys14) and an internal Asn-aromatic motif (NNNxxNYQ, residues 2-9) appeared to be required for fibril formation. The fibril formation of the CT-14 peptide in this case involved an interaction between charge pair as well as stacking interactions between aromatic rings, as previous reports indicated that π-bonding between adjacent aromatic rings and salt bridges between charge pairs served to control and stabilize the structure of β-amyloid-like fibrils. Taken together, these results strongly suggested that both terminal charged residues (Asp1 and Lys14) and the NNN and NYQ motifs (residues 2-4 and 7-9 in CT-14 peptide, respectively) were required for fibril formation.

Structural Assessment of the Fibrillar CT-14 Peptide

Figure 14:
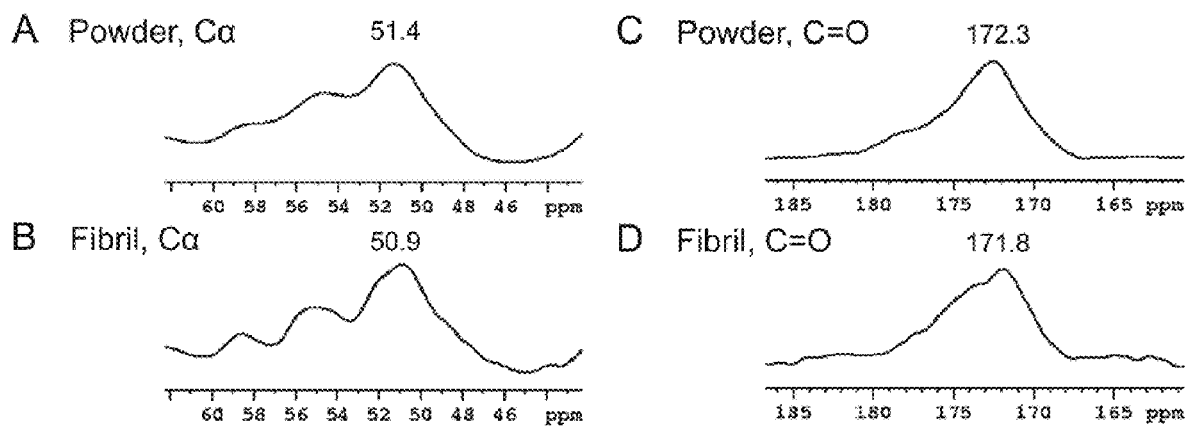
FIG. 14 shows the structural features of the fibril-forming segment CT-14. (A) The powdered CT-14 peptide $^{13}C\alpha$ chemical shift was measured and data were collected by solid-state NMR. (B) The CT-14 peptide was incubated in 10 mM sodium citrate buffer (pH 4.5) at 72 h to assemble insoluble fibrils. The $^{13}C\alpha$ chemical shift of fibrillar CT-14 peptide was measured by solid-state NMR. (C) The powdered CT-14 peptide $^{13}C=O$ chemical shift was measured by solid-state NMR. (D) The CT-14 peptide was incubated in 10 mM sodium citrate buffer (pH 4.5) for 72 h to assemble insoluble fibrils. The $^{13}C=O$ chemical shift of fibrillar CT-14 peptide was measured by solid-state NMR.

Recently, amyloid fibrils characterized by x-ray diffraction and solid state NMR had been established. Therefore, powdered and fibrillar CT-14 peptide were also examined to measure $^{13}$C-CP/MAS by solid-state NMR (FIG. 14A-14D). The positive deviation from random coil chemical shifts was indicative of an α-helical conformation whereas a negative deviation was indicative of a β-sheet conformation. The spectral peak of the $^{13}$Cα chemical shift in the powdered CT-14 peptide appeared at 51.4 ppm (FIG. 14A), whereas that of the fibrillar CT-14 peptide was negatively deviated to 50.9 ppm (FIG. 14B). Moreover, the spectral peaks of the $^{13}$C=O chemical shift in powdered and fibrillar forms appeared at 172.3 and 171.8 ppm, respectively (FIGS. 14C and 14D). The data also displayed negative deviation as expected for generation of the β-sheet conformation. In conclusion, the present invention demonstrated that the CT-14 peptide governs β-sheet-rich fibril formation of SBD while key factors were the interaction of the terminal charged amino acid pair and the interaction of the NNN and NYQ motifs.

Effects of Buffer and pH on CT-14 Peptide Fibril Formation

Figure 15:
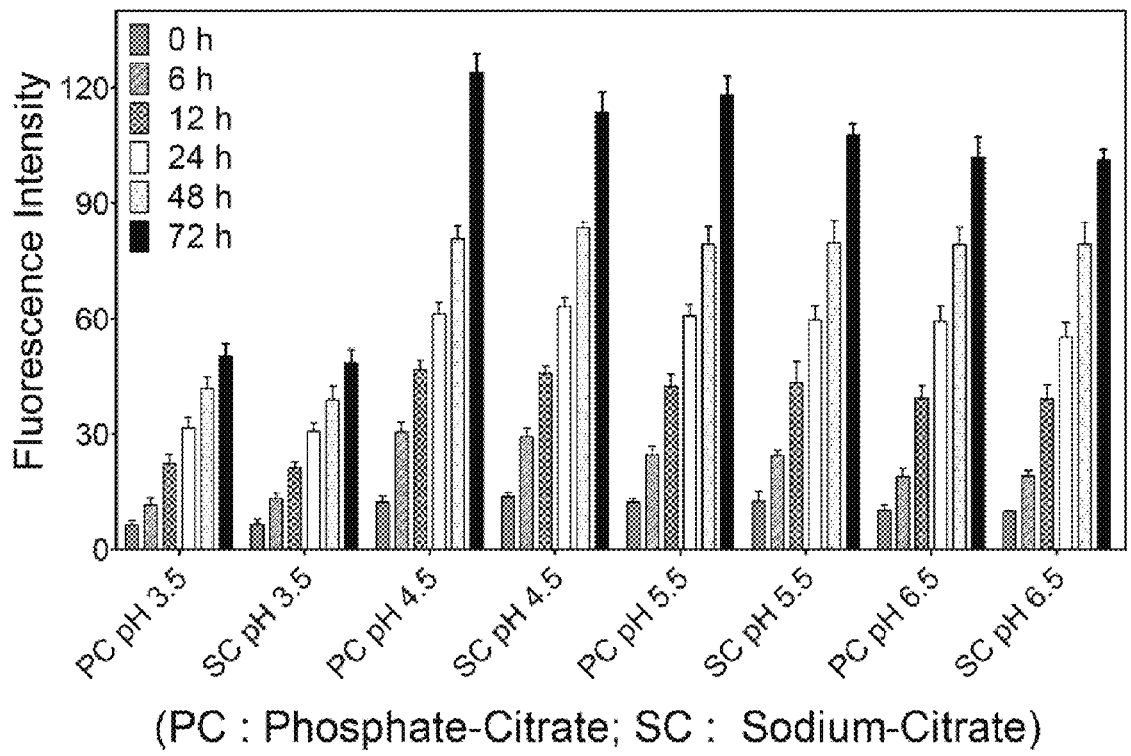
FIG. 15 shows the buffer and pH-dependence of CT-14 peptide fibril formation. (A) CT-14 peptide (100 µM) was incubated in 10 mM sodium citrate or 10 mM phosphate-citrate buffer at different pH values (pH 3.5, 4.5, 5.5, and 6.5), then incubated with ThT at 37° C. for 10 min. ThT fluorescence emission spectra were measured by spectrofluorometry scanning from 470 to 630 nm. (B) CT-14 peptide (100 µM) was incubated in 10 mM phosphate-citrate buffer over a pH range between 2.0 and 8.0, then incubated with ThT at 37° C. for 10 min. The ThT fluorescence spectra were collected from 470 to 630 nm.
Figure 15:
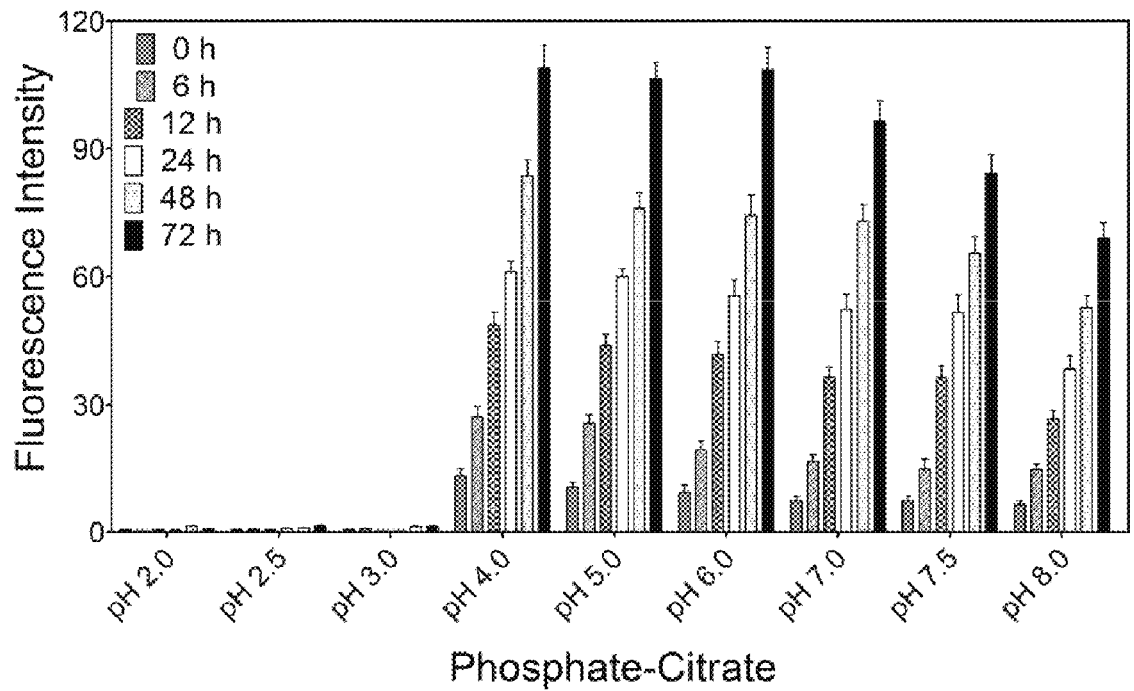

It is known that pH variation could change the net charge of a peptide and thus influenced subsequent β-amyloid-like fibril formation. In the present invention, the CT-14 peptide was initially dissolved in 10 mM sodium-citrate (pH 4.5) and fibril formation was observed upon heat treatment. Because the working pH value of sodium citrate as a buffer solution ranged from 3.0 to 6.6, buffer pH values of 3.5, 4.5, 5.5, and 6.5 for fibril formation were examined. In addition, due to the wider buffering range of phosphate-citrate buffer, the pH values 2.0, 2.5, 3.0, 3.5, 4.0, 4.5, 5.0, 5.5, 6.0, 6.5, 7.0, and 8.0 were also tested. FIGS. 15A and 15B showed attenuated emission fluorescence intensity at 482 nm from ThT binding to the CT-14 peptide dissolved in either 10 mM sodium-citrate or 10 mM phosphate-citrate at pH 3.5, a pH value near the pI of Asp; this reduced intensity was due to a change in the crucial terminal negative charge property of CT-14. As the pH was increased to 4.5, 5.5, or 6.5, the fluorescence intensity for the CT-14 peptide became stronger than that at pH 3.5 at all time points examined. Furthermore, when phosphate-citrate buffer at pH 3.0 and lower was examined, the fluorescence intensity significantly declined to almost zero, indicating no fibril formation at pH 2.0, 2.5, and 3.0. Similar fluorescence intensities were measured for CT-14 at all pH values ranging from 4.0 to 7.0. However, the ThT signals decreased approximately 20 to 30% in buffers at pH 7.5 and 8.0, presumably due to neutralization of the Lys charge near its pI. pH values higher than 7.5 significantly influenced the ionic property of the C-terminal Lys residue in the CT-14 peptide, which in turn influenced the formation of β-sheet-rich fibrils. Furthermore, when Tris buffer was adjusted to pH values above 8.0, low emission fluorescence intensity at 482 nm was detected at 72 h (data not shown), indicating that it changed the ionic property of the Lys14 residue and abolished fibril formation. Taken together, maintenance of the crucial charge pair between Asp and Lys in the CT-14 peptide in a buffer system with a pH range between 4.0 and 7.0 appeared to be required for fibril biogenesis in SBD.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein.

Modifications therein and other uses will occur to those skilled in the art. These modifications are encompassed within the spirit of the invention and are defined by the scope of the claims.

What is claimed is:

1. A fibril-forming 14-residue peptide consisting of $X_1NNNX_2X_3NYQX_4X_5X_6X_7X_8$, wherein the $X_1$ and $X_8$ mean a pair of opposite charged amino acid residues, and the $X_2$, $X_3$, $X_4$, $X_5$, $X_6$, or $X_7$ means an amino acid residue, wherein if the $X_8$ is K, the $X_1$ is D; if the $X_8$ is D, the $X_1$ is K; the $X_2$ is S or A; the $X_3$ is A; the $X_4$ is V or A; the $X_5$ is S or A; the $X_6$ is T or A, and the $X_7$ is S or A.

2. The peptide of claim 1, which is SEQ ID NO: 7.

3. A method of producing an amyloid-like fibril, comprising dissolving the peptide of claim 1 in a solution with pH value ranges from 4.0 to 7.0 upon heat treatment for mature fibril formation, wherein the amyloid-like fibril is composed of the dissolving peptide, and the appearance of the amyloid-like fibril is straight and/or branched, and the thickness and the lenghth of the amyloid-like fibril is proportional to the formation time.

4. The method of claim 3, wherein the solution is 10 mM sodium-citrate or phosphate-citrate buffer.

5. The method of claim 3, wherein the fibril is applied to carbohydrate separation, drug delivery, biodegradable three-dimensional scaffold construction, nanowire production, or nanotube formation.

* * * * *